(12) United States Patent
Mendez et al.

(10) Patent No.: US 7,569,687 B2
(45) Date of Patent: Aug. 4, 2009

(54) PROCESSES FOR THE SYNTHESIS OF ROCURONIUM BROMIDE

(75) Inventors: Juana Araceli Mendez, Coyoacan (MX); Marco A. De La Mora, Capultitlan (MX); Angel A. Rodriguez, Chapultepec (MX); Efrain Barragán, Toluca, Edo. (MX); Hugo Herrera, Ampliacion Izcalli Ecatepec (MX); Alejandro Guillen, Xonacatlan (MX)

(73) Assignee: Sicor, Inc., Irvine, CA (US)

( * ) Notice: Subject to any disclaimer, the term of this patent is extended or adjusted under 35 U.S.C. 154(b) by 82 days.

(21) Appl. No.: 11/521,282

(22) Filed: Sep. 13, 2006

(65) Prior Publication Data

US 2007/0117975 A1 May 24, 2007

Related U.S. Application Data

(60) Provisional application No. 60/717,122, filed on Sep. 13, 2005, provisional application No. 60/752,671, filed on Dec. 19, 2005, provisional application No. 60/752,435, filed on Dec. 20, 2005, provisional application No. 60/776,322, filed on Feb. 23, 2006, provisional application No. 60/784,746, filed on Mar. 21, 2006.

(51) Int. Cl.
*C07D 265/28* (2006.01)
*C07D 295/00* (2006.01)

(52) U.S. Cl. .................................................... 544/98

(58) Field of Classification Search .................. None
See application file for complete search history.

(56) References Cited

U.S. PATENT DOCUMENTS

| 3,553,212 | A | 1/1971 | Hewett et al. |
| 4,447,425 | A | 5/1984 | Carlyle et al. |
| 4,894,369 | A | 1/1990 | Sleigh et al. |
| 5,591,735 | A | 1/1997 | Tuba et al. |
| 5,808,051 | A | 9/1998 | Magni et al. |
| 5,817,803 | A | 10/1998 | Magni et al. |
| 6,090,957 | A | 7/2000 | Magni et al. |
| 2005/0159398 | A1 | 7/2005 | Adar et al. |
| 2006/0009485 | A1 | 1/2006 | Friedman et al. |
| 2006/0058275 | A1 | 3/2006 | Friedman et al. |
| 2006/0058276 | A1 | 3/2006 | Friedman et al. |
| 2007/0265237 | A1 | 11/2007 | Mendez et al. |

FOREIGN PATENT DOCUMENTS

| DE | 19903894 | 8/2000 |
| EP | 0 287 150 A1 | 10/1988 |
| EP | 0 288 102 A1 | 10/1988 |
| EP | 0 608 495 A2 | 8/1994 |
| KR | 20070083226 A | 8/2007 |
| WO | WO-2005/068487 A2 | 7/2005 |
| WO | WO-2007/073424 | 6/2007 |

OTHER PUBLICATIONS

Buckett, W. R., et al., "Pancuronium Bromide and Other Steroidal Neuromuscular Blocking Agents Containing Acetylcholine Fragments", Journal of Medicinal Chemistry, 1973, vol. 16, No. 10, pp. 1116-1124.
Strobel, H.A. & Heineman, W.R., Chemical Instrumentation: A Systematic Approach 922, 953 (3d ed., Wiley & Sons, New York 1989).
International Search Report and Written Opinion of the International Searching Authority for PCT/US2006/035828 dated Mar. 6, 2007.
Cameron, Kenneth S., et al., Magnetic Resonance in Chemistry, 2002, vol. 40, pp. S106-S109.
Cameron, Kenneth S., et al., Organic Letters, 2002, vol. 4, No. 20, pp. 3403-3406.
Cameron, Kenneth S., et al., Magnetic Resonance in Chemistry, 2002, vol. 40, No. 4, pp. 251-260.
Adam, Julia M., et al., Journal of Medicinal Chemistry, 2002, vol. 45, No. 9, pp. 1806-1816.
Van Montfoort, Jessica E., et al., Journal of Pharmacology and Experimental Therapeutics, 2001, vol. 298, No. 1, pp. 110-115.
Gutteck-Amsler, Ursula, et al., Clinical Chemistry, 2000, vol. 46, No. 9, pp. 1413-1414.

*Primary Examiner*—James O Wilson
*Assistant Examiner*—Noble Jarrell
(74) *Attorney, Agent, or Firm*—Kenyon & Kenyon LLP

(57) ABSTRACT

The invention encompasses processes for synthesizing 1-[17β-acetyloxy-3α-hydroxy-2β-(4-morpholinyl)-5α-androstan-16β-yl]-1-(2-propenyl)pyrrolidinium bromide (rocuronium bromide) and intermediates thereof.

13 Claims, 7 Drawing Sheets

PROCESSES FOR THE SYNTHESIS OF ROCURONIUM BROMIDE

RELATED APPLICATIONS

This application claims the benefit of U.S. provisional application Ser. Nos. 60/717,122, filed on Sep. 13, 2005; 60/752,671, filed on Dec. 19, 2005; 60/752,435, filed on Dec. 20, 2005; 60/776,322, filed on Feb. 23, 2006; and 60/784,746, filed on Mar. 21, 2006, herein incorporated by reference.

FIELD OF THE INVENTION

The invention encompasses processes for synthesizing 1-[17β-acetyloxy-3α-hydroxy-2β-(4-morpholinyl)-5α-androstan-16β-yl]-1-(2-propenyl)pyrrolidinium bromide (rocuronium bromide) and intermediates thereof.

BACKGROUND OF THE INVENTION

1-[17β-(acetyloxy)-3α-hydroxy-2β-(4-morpholinyl)-5β-androstan-16β-yl]-1-(2-propenyl)pyrrolidinium bromide (rocuronium bromide) of formula I, has the following structure:

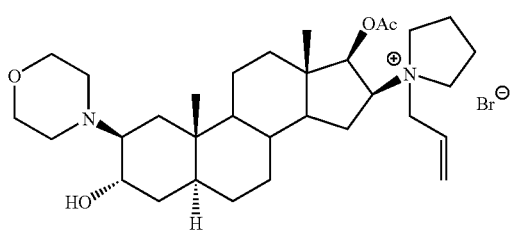

I with a formula of $C_{32}H_{53}BrN_2O_4$ and a molecular weight of 609.70. Rocuronium bromide is used as a nondepolarizing neuromuscular blocking agent with a rapid to intermediate onset depending on dose and intermediate duration. It acts by competing for cholinergic receptors at the motor end-plate. This action is antagonized by acetylcholinesterase inhibitors, such as neostigmine and edrophonium.

Rocuronium bromide of formula I is marketed under the name ZEMURON® and is supplied as a sterile, nonpyrogenic, isotonic solution that is clear, colorless to yellow/orange, for intravenous injection only.

The preparation of rocuronium bromide is disclosed in U.S. Pat. Nos. 5,817,803 and 4,894,369, and in U.S. publication No. 2005/0159398.

U.S. Pat. No. 4,894,369 ("'369 patent") discloses the preparation of Rocuronium bromide via 2α,3α-epoxy-16β-(1-pyrrolidinyl)-5α-androstan-17β-ol of formula II:

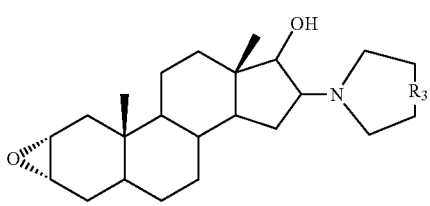

II wherein $R_3$ is C, N—$CH_3$ or a direct C—C bond. The yield is modest (around 60% w/w yield). The patent discloses the reaction of 2α,3α-epoxy-16β-(1-pyrrolidinyl)-5α-androstan-17β-ol with morpholine in the presence of water to yield 2β-(4-morpholinyl)-16β-(1-pyrrolidinyl)-5α-androstan-3α,17β-diol. The step is conducted for a reaction time of three days after which the solvents are removed by evaporation and the final product is crystallized from acetone followed by further recrystallization from methanol.

Thereafter, 2β-(4-morpholinyl)-16β-(1-pyrrolidinyl)-5α-androstan-3α,17β-diol is reacted with an acetylating reagent to obtain 2β-(4-morpholinyl)-16β-(1-pyrrolidinyl)-5α-androstan-3α-ol, 17β-acetate. In this acetylation process the product is obtained in low yields of about 48%, comprising a process of purifying from the remaining starting diol, and diacetate side product, by column chromatography followed by crystallization from a mixture of diethyl ether and n-hexane. See '369 patent, col. 5, ll. 31-50 (example 7).

Finally, the mono-quaternary ammonium compound, rocuronium bromide, is prepared by a reaction of the monoacetate derivative and a large excess of allyl bromide (8.7 equivalents) in a pressure bottle at room temperature for 22 hours. See id. at col. 8, ll. 27-46 (example 23). The product is purified by column chromatography on alumina and the combined pure fractions are subsequently crystallized from dichloromethane-diethylether to yield pure rocuronium bromide.

U.S. publication No. 2005/0159398 ("'398 publication") discloses the preparation of a derivative of Rocuronium through a bis-acetylated intermediate. The bis-acetylated compound undergoes a selective de-acetylation reaction to give a mono-acetate product, which is further purified by two crystallizations to give the desired product in yields of about 52%. See '398 publication, p. 8, ¶¶ 112-115.

Each purification step reduces yield, increases the cost of production, and increases manufacturing time. Thus, processes that reduce cost and manufacturing time, while concurrently increasing the product yield and purity are highly desirable. Also desirable, are processes that simplify the production process. The process of the present invention addresses these shortcomings of the prior art.

SUMMARY OF THE INVENTION

One embodiment of the invention encompasses isolated compound VI of the following structure.

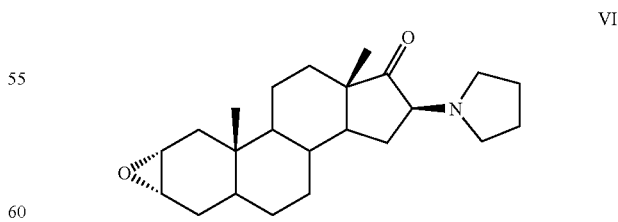

VI

Another embodiment of the present invention encompasses crystalline compound VI.

Yet another embodiment of the invention encompasses a process for increasing the isomeric ratio of Compound VI to Compound VI-a of the following structure

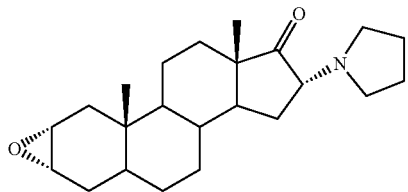

VI-a comprising combining a starting Compound VI containing about 10% to about 40% area by HPLC of Compound VI-a with a water miscible organic solvent to obtain a suspension; stirring the suspension at a temperature of about 60° C. to about 80° C. for a sufficient amount of time to obtain a solution; adding water to the solution to form a suspension; and isolating Compound VI from the mixture; wherein the isolated Compound VI contains no more than about 3% area by HPLC of Compound VI-a.

One embodiment of the invention encompasses a process for preparing Rocuronium bromide of formula I (hereinafter "Roc")

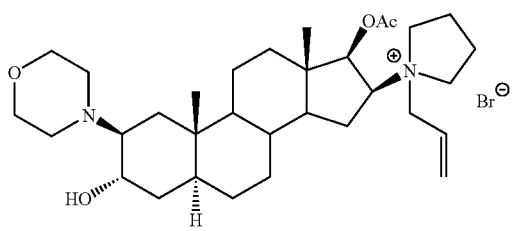

I by preparing Compound VI with less than about 10% area by HPLC of Compound VI-a by the process of the present invention, and converting it to Rocuronium bromide.

The invention also encompasses a process for preparing Compound IV:

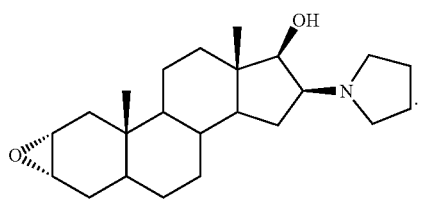

IV comprising forming a solution of Compound VI with less than about 10% of compound VI-a, and a water miscible organic solvent optionally combined with a water immiscible organic solvent; adding at least one reducing agent to the solution at a temperature of about −15° C. to about 10° C. to obtain a mixture; stirring the mixture at a temperature of about 20° C. to about 24° C.; and isolating Compound IV from the mixture having a purity of at least 85% area by HPLC.

One embodiment of the present invention encompasses a process for preparing Roc of formula I by preparing compound IV having a purity of at least 85% area by HPLC as described above, and converting it to Roc of formula I.

Another embodiment of the invention encompasses a process for preparing Compound VII

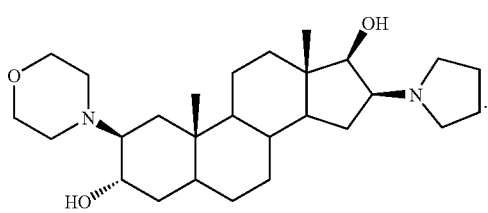

VII comprising forming a suspension of Compound IV, morpholine, and at least one acid catalyst; stirring the suspension at a temperature of about 100° C. to about reflux for about 24 hours to about 48 hours; and isolating Compound VII from the suspension.

Yet another embodiment of the present invention encompasses a process for preparing Roc of formula I by preparing compound VII as described above, and converting it to Roc of formula I.

One embodiment of the invention encompasses a process for the preparation of Compound VIII

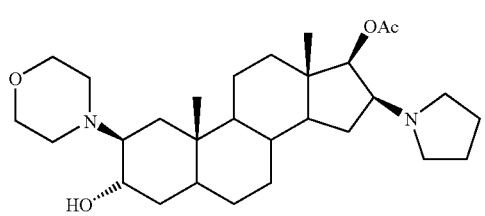

VIII comprising combining Compound VII, a polar organic solvent, and at least one acetylating reagent with at least one base to obtain a mixture; and isolating Compound VIII from the mixture.

Another embodiment of the invention encompasses a process for preparing rocuronium bromide comprising a process for preparing rocuronium bromide from compound VIII comprising combining Compound VIII, a polar aprotic organic solvent, allyl bromide, and at least one inorganic base to obtain a mixture; and isolating rocuronium bromide.

The isolated rocurominum bromide may be purified by a process comprising: dissolving the isolated rocuronium bromide in at least one polar aprotic organic solvent to form a solution; adding a decolorizing agent optionally combined with a base to the solution to form a first suspension; filtering the first suspension; adding the resulting filtrate to an antisolvent; stirring vigorously to obtain a second suspension; recovering wet solid Rocuronium bromide from the second suspension; and drying the wet Rocuronium bromide at a temperature of no more than about 35° C.

Yet another embodiment of the present invention encompasses a process for the preparation of the quaternary ammonium salt, Roc, of formula I

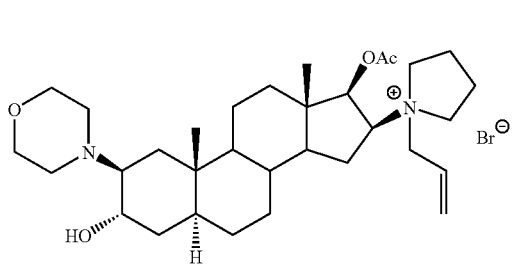

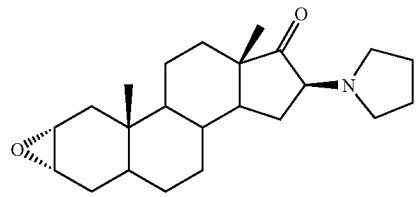

comprising combining a starting Compound VI containing about 10% to about 40% area by HPLC of Compound VI-a with a water miscible organic solvent to obtain a suspension; stirring the suspension at a temperature of about 60° C. to about 80° C. to obtain a solution; forming a suspension by adding water to the solution; isolating Compound VI from the suspension, wherein the isolated Compound VI is with less than about 3% area by HPLC of Compound VI-a; forming a solution of Compound VI with less than about 3% of compound VI-a, and at least one water miscible organic solvent; adding at least one reducing agent to the solution at a temperature of about −15° C. to about 10° C. to obtain a mixture; stirring the mixture at a temperature of about 20° C. to about 24° C.; isolating Compound IV from the mixture having a purity of at least 85% area by HPLC, preferably above 90%; forming a suspension of Compound IV, morpholine, and at least one acid catalyst; stirring the suspension at a temperature of about 100° C. to about reflux for about 24 hours to about 48 hours; isolating Compound VII from the suspension; combining Compound VII, a polar organic solvent, and at least one acetylating reagent with at least one base to obtain a mixture; isolating Compound VIII from the mixture; combining Compound VIII, a polar aprotic organic solvent, allyl bromide, and at least one inorganic base to obtain a mixture; and isolating rocuronium bromide.

DETAILED DESCRIPTION OF THE INVENTION

The invention encompasses isolated compound VI of the following structure.

Figure 4:
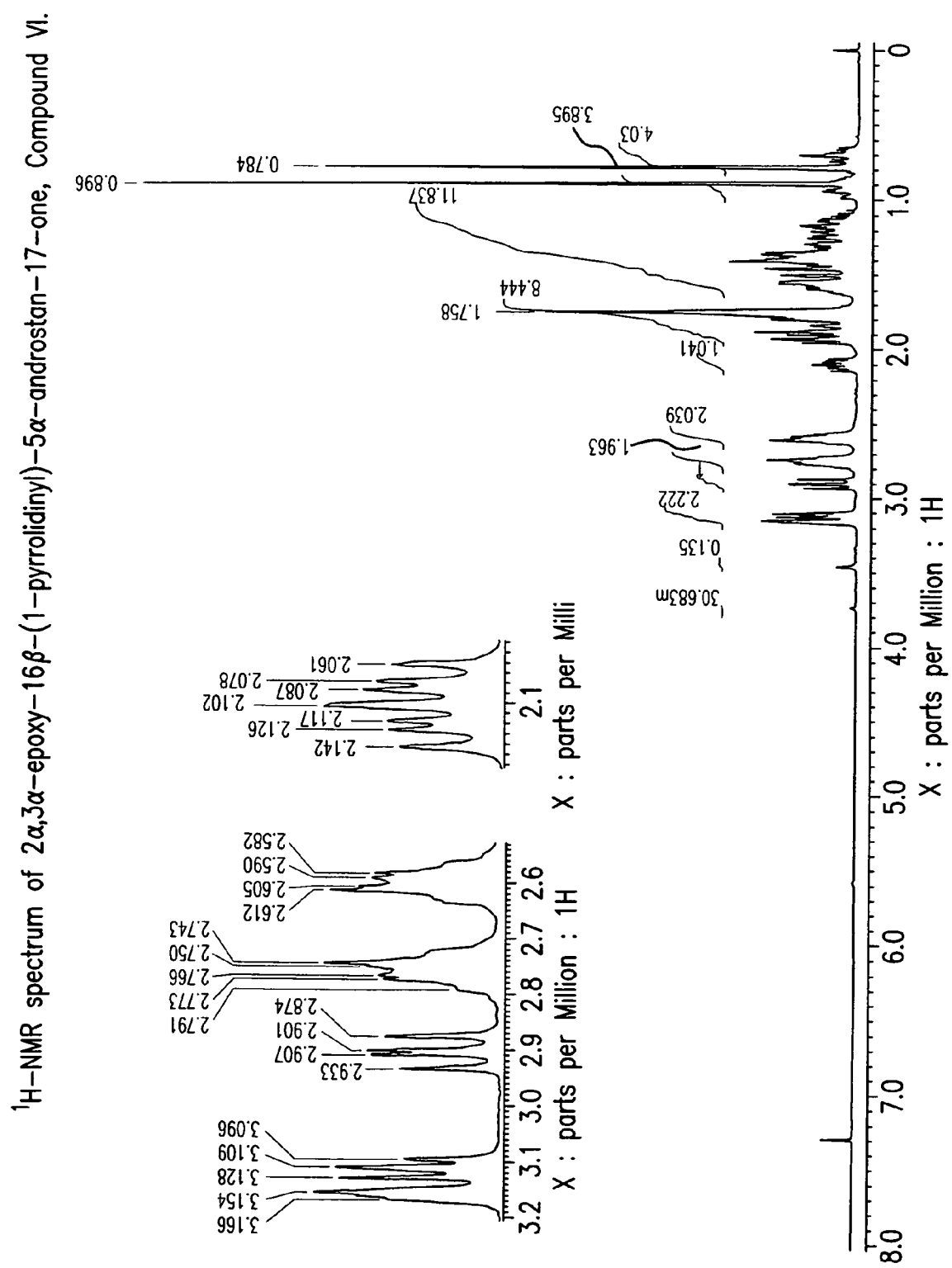
FIG. 4 illustrates the $^1$H-NMR spectrum of 2α,3α-epoxy-16β-(1-pyrrolidinyl)-5α-androstan-17-one, Compound VI.
Figure 5:
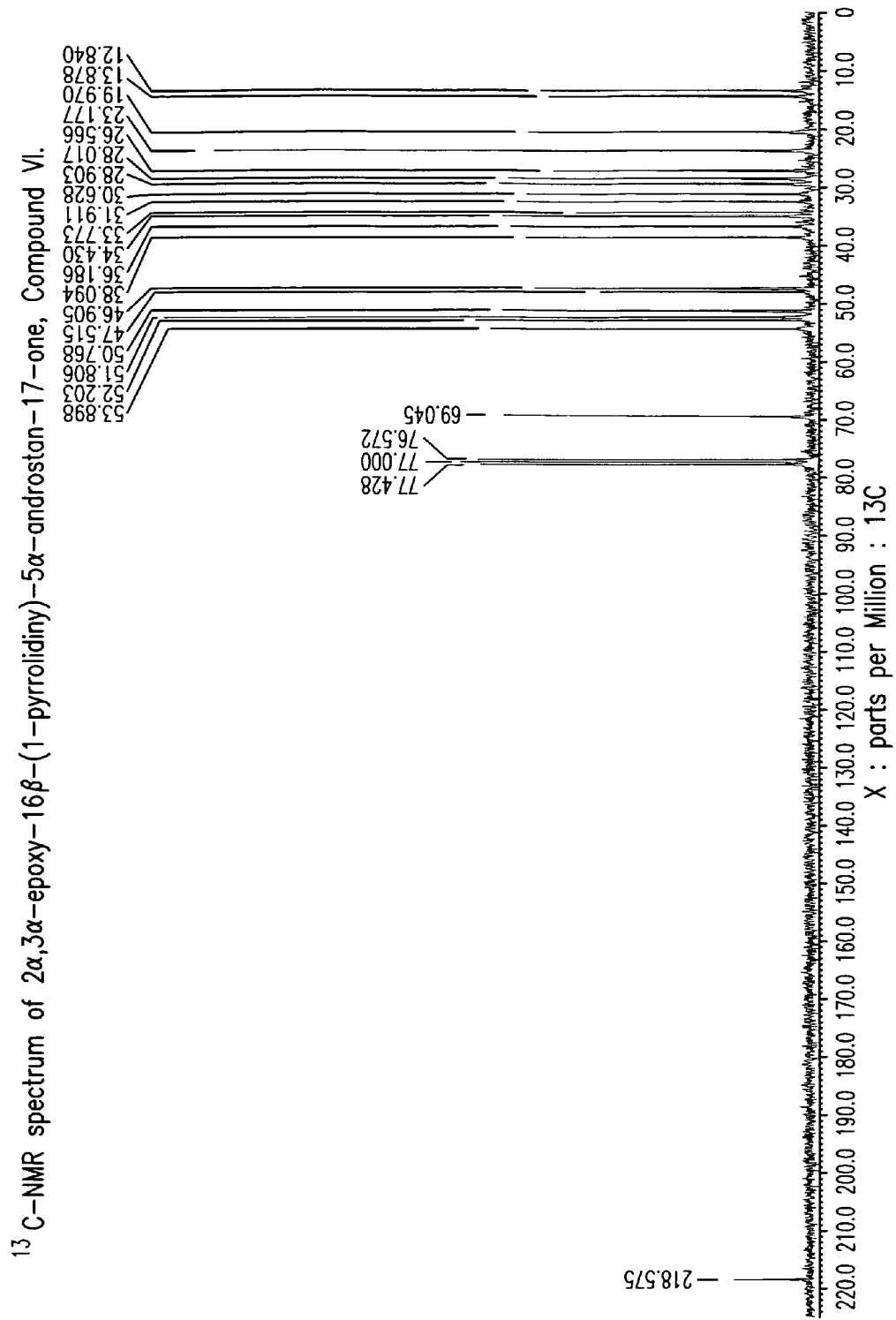
FIG. 5 illustrates the $^{13}$C-NMR spectrum of 2α,3α-epoxy-16β-(1-pyrrolidinyl)-5α-androstan-17-one, Compound VI.
Figure 6:
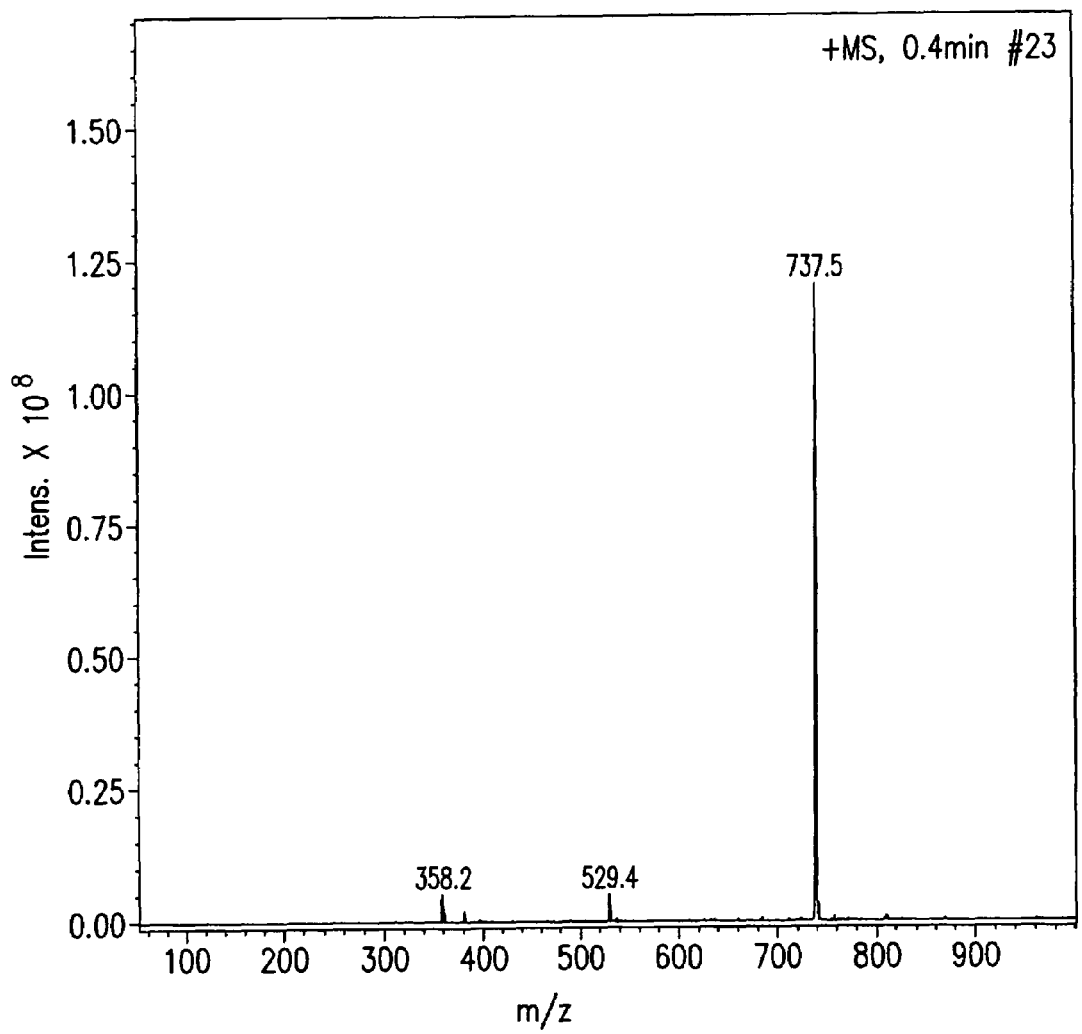
FIG. 6 illustrates the MS spectrum of 2α,3α-epoxy-16β-(1-pyrrolidinyl)-5α-androstan-17-one, Compound VI.
Figure 7:
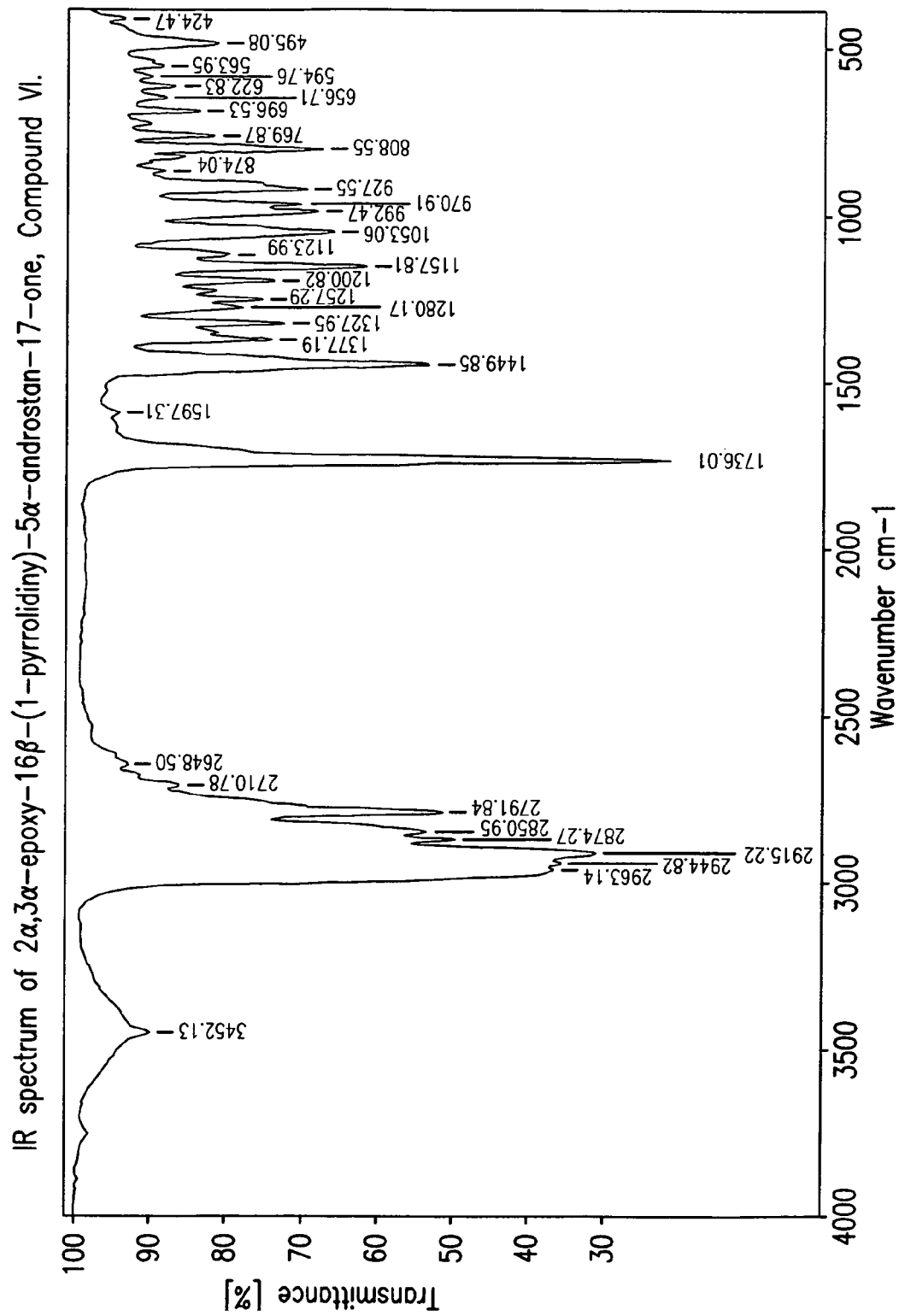
FIG. 7 illustrates the IR spectrum of 2α,3α-epoxy-16β-(1-pyrrolidinyl)-5α-androstan-17-one, Compound VI.

The isolated compound of formula VI may be characterized by data selected from: a $^{13}$C-NMR spectrum having carbon chemical shifts at about 218.3, 69, 53.9, 52.2, 51.9, 50.8, 47.5, 46.9, 38.1, 36.2, 34.4, 33.8, 31.9, 30.6, 28.9, 28, 26.6, 23.2, 20, 13.9 and 12.9 ppm; a $^{13}$C-NMR spectrum substantially as depicted in FIG. 5; an $^1$H-NMR spectrum having hydrogen chemical shifts at about 3.17-3.09, 2.92, 2.79, 2.64, 2.1, 1.95-0.66, 0.9 and 0.75 ppm; an $^1$H-NMR spectrum substantially as depicted in FIG. 4; a mass spectrum (FAB(+), m/z) having a peak of MH+ at about 358.2; a mass spectrum substantially as depicted in FIG. 7; an IR spectrum having peaks at about 1736, 3452 and 1157 cm−1, and an IR spectrum substantially as depicted in FIG. 8.

Figure 1:
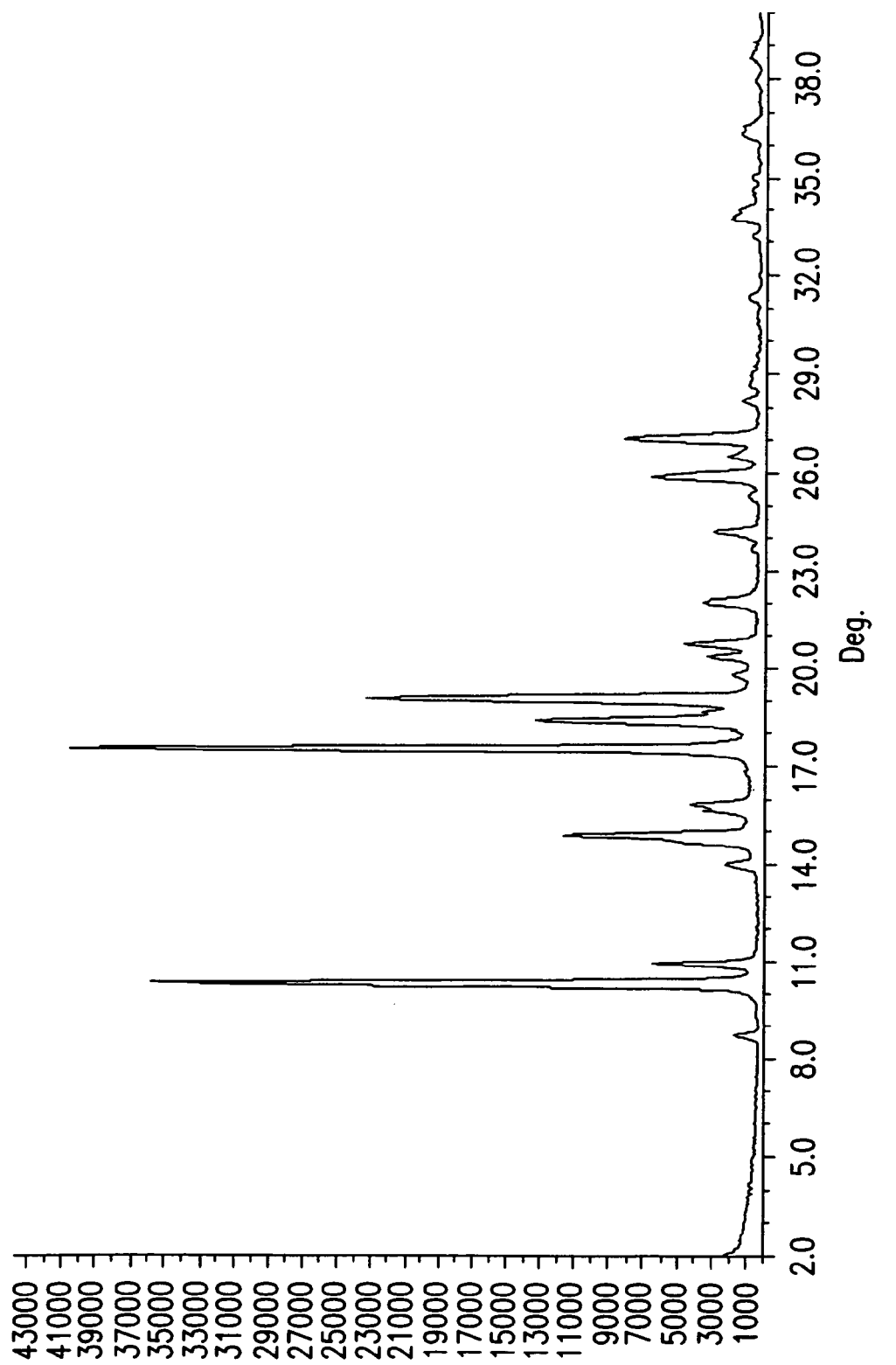
FIG. 1 illustrates the X-ray diffraction pattern of 2α,3α-epoxy-16β-(1-pyrrolidinyl)-5α-androstan-17-one, Compound VI.
Figure 2:
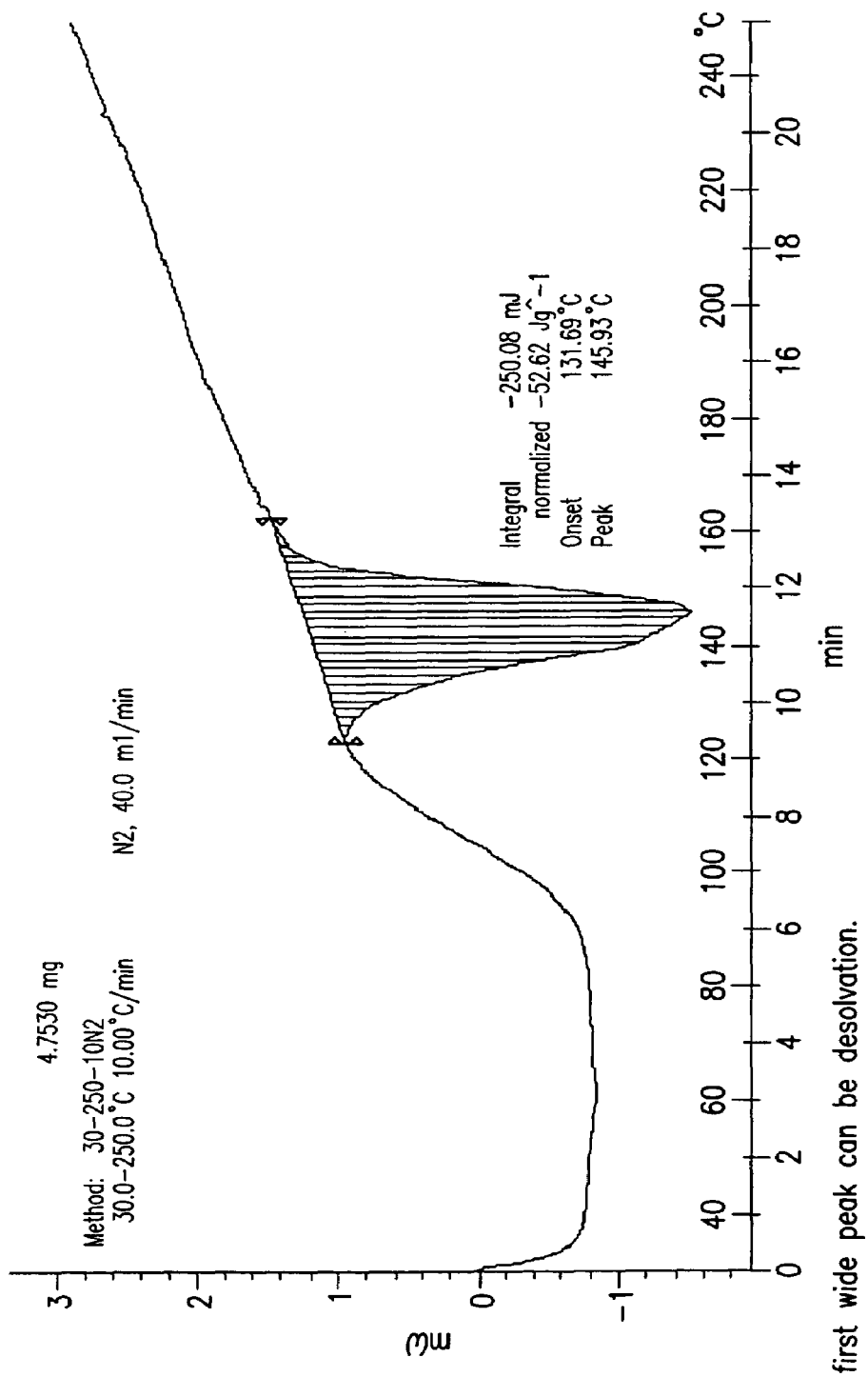
FIG. 2 illustrates the DSC curve for 2α,3α-epoxy-16β-(1-pyrrolidinyl)-5α-androstan-17-one, Compound VI.
Figure 3:
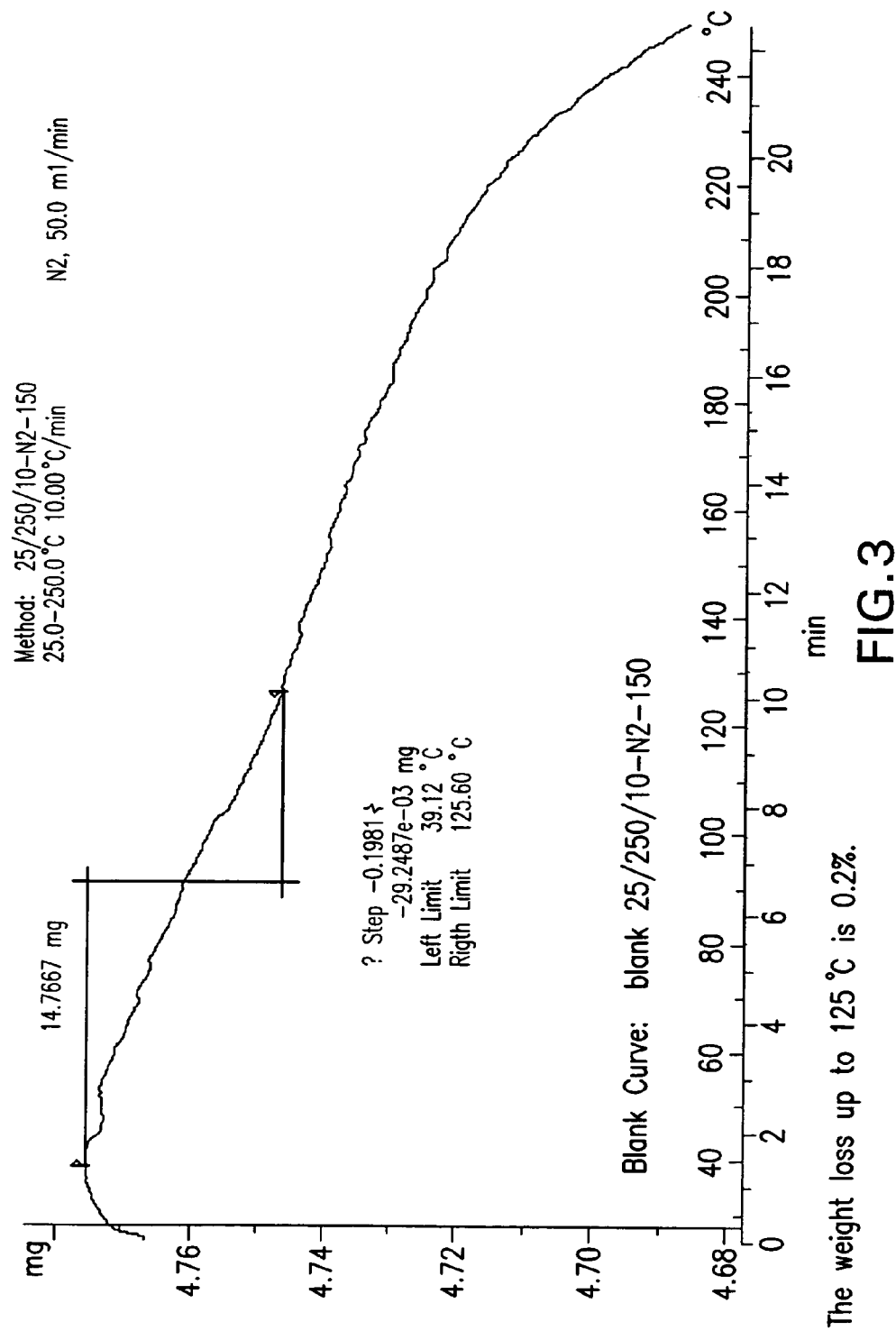
FIG. 3 illustrates the TGA curve for 2α,3α-epoxy-16β-(1-pyrrolidinyl)-5α-androstan-17-one, Compound VI.

The invention also encompasses crystalline compound VI. The crystalline compound VI may be characterized by powder X-ray diffraction peaks at 10.3, 14.8, 17.5, 18.4 and 19 degrees two-theta, ±0.1 degrees two-theta. The said crystalline compound VI may also be characterized by data selected from a group consisting of: a powder X-ray diffraction peaks at about 10.9, 20.7, 22, 24.1, 25.9 and 27 degrees two-theta, ±0.1 degrees two-theta; a powder X-ray diffraction substantially as depicted in FIG. 1; a weight loss of about 0.2% by weight, as determined by TGA analysis; a TGA curve substantially as depicted in FIG. 3; a DSC having an endothermic peak at about 146° C.; a DSC curve substantially as depicted in FIG. 2, and by a melting point of about 155° C.

The invention further encompasses processes for the synthesis of rocuronium bromide using a process that increases yields while reducing the impurity profile of the intermediates and final product. In part, the impurities are reduced when 2 mol equivalents of pyrrolidine are allowed to react with the Compound V, defined below, to avoid the production of undesired side products and/or unnecessary purification steps during intermediate synthesis. Furthermore, the recovery of the product is much more facile leading to a product containing only a small amount of by products, such as compounds of Formula VI-a and/or VI-c:

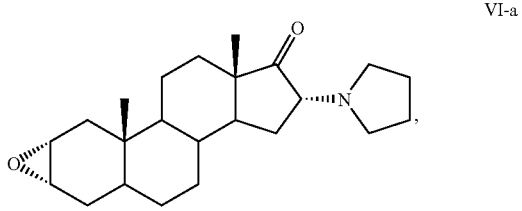

-continued

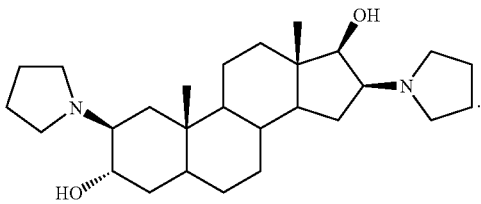

VI-c

As used herein, the term "base" refers to a substance that accepts one or more protons during a chemical reaction. The term "strong base" refers to a substance having a high affinity to H⁺ including, but not limited to, NaOH, NaHCO$_3$, Na$_2$CO$_3$, KOH, KHCO$_3$, or K$_2$CO$_3$.

As used herein, the term "wet solvent," refers to a solvent containing a volume of about 1% to about 7% of water in the total volume of solvent.

The process for the preparation of Compound VI

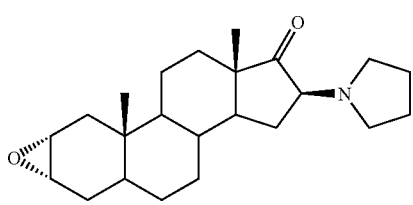

VI comprises combining 2α,3α-epoxy-5α-androstan-16β-ol-17-one, Compound V, and pyrrolidine in a water miscible organic solvent at a temperature of about 40° C. to about reflux to obtain a mixture; stirring the mixture at a temperature of about 40° C. to about reflux for about 30 minutes to about an hour to obtain Compound VI; and isolating Compound VI.

Compound V can be prepared by reacting a solution of 2α,3α,16α,17α-bisepoxy-5α-androstan-17β-acetate (Compound III) with an aqueous solution of a strong base in a water miscible organic solvent at a temperature of about 40° C. to about reflux. The water miscible organic solvent can be any of those described below for the synthesis of Compound VI. However, the more preferred water miscible organic solvent is methanol and the more preferred base is NaOH.

Alternatively, Compound V can be made in situ prior to the reaction with pyrrolidine. Thus, the reaction described above may be performed sequentially wherein 2α,3α,16α,17α-bisepoxy-5α-androstan-17β-acetate (Compound III) is allowed to react with an aqueous solution of a strong base to yield Compound V, which then is allowed to react with pyrrolidine to yield Compound VI. Thus, Compound V is made without intermediate isolation prior to synthesis of Compound VI.

Compound III can be obtained, for example, according to the process disclosed by Buckett, W. R., "Pancuronium bromide and other steroidal neuromuscular blocking agents containing acetylcholine fragments," *J. Med. Chem.*, 1973, 16(10), pp.1116-1124.

Preferably, the water miscible organic solvent is at least one straight or branched C$_1$-C$_5$ alcohol. Preferably, the C$_1$-C$_5$ alcohol is a C$_1$-C$_3$ alcohol. A preferred C$_1$-C$_3$ alcohol is methanol, ethanol or 2-propanol. More preferably, the C$_1$-C$_3$ alcohol is methanol.

Preferably, combining 2α,3α-epoxy-5α-androstan-16β-ol-17-one, Compound V, and pyrrolidine in a water miscible organic solvent is performed at a temperature of about 40° C. to about 65° C., more preferably, of about 60° C. to about 65° C.

The pyrrolidine should be present in sufficient amount to yield Compound VI without yielding large amounts of the Compound VI-c. Preferably, the pyrrolidine is present in an amount of 2 or less mole equivalents per mole equivalent of Compound III.

Preferably, the mixture is stirred at a temperature of about 40° C. to about 65° C., more preferably, of about 60° C. to about 65° C.

Preferably, the mixture is stirred for about 30 to about 120 minutes. Compound VI may be recovered by any method known to the skilled artisan. Such methods, include, for example, adding ice-water to the mixture, and filtering the precipitated product.

The reaction of 2α,3α-epoxy-5α-androstan-16β-ol-17-one, Compound V, and pyrrolidine typically produces a mixture of isomers Compound VI and Compound VI-a:

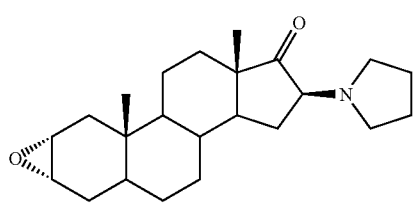

VI

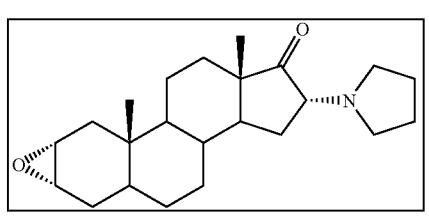

VI-a

The invention further encompasses a process for increasing the isomeric ratio of Compound VI over Compound VI-a comprising combining a starting Compound VI containing about 10% to about 40% area by HPLC of Compound VI-a with a water miscible organic solvent to obtain a suspension; stirring the suspension at a temperature of about 60° C. to about 80° C. for a sufficient amount of time to obtain a solution; adding water to the solution to form a suspension; and isolating Compound VI from the mixture; wherein the isolated Compound VI contains no more than about 3% area by HPLC of Compound VI-a.

Typically, the starting Compound VI may contain about 10% to about 40% area by HPLC of Compound VI-a. Preferably, the starting Compound VI contains about 15% to about 30% area by HPLC of Compound VI-a. More preferably, the starting Compound VI contains about 10% to about 20% area by HPLC of Compound VI-a, most preferably, the isolated compound of formula VI contains about 12% to about 18% area by HPLC of compound of formula VI-a.

Preferably, the isolated Compound VI contains less than 3% area by HPLC of Compound VI-a, more preferably, the less than about 2% area by HPLC, most preferably, less than 1% area by HPLC.

Preferably, the water miscible organic solvent is at least one $C_{1-4}$ alcohol, more preferably, methanol, ethanol, propanol, isopropanol or butanol. Preferably, the $C_{1-4}$ alcohol is methanol.

Preferably, the suspension is stirred at a temperature of about 50° C. to about 70° C.

Preferably, the water is added drop-wise, more preferably, over a period of about 90 minutes.

Preferably, the water is added while maintaining the mixture at a temperature above 60° C.

Preferably, the water is added in an amount of about 3 to about 4 volumes of the volume of the water miscible organic solvent, more preferably, of about 3 volumes of the volume of the water miscible organic solvent.

Preferably, compound VI containing less than about 3% area by HPLC of compound VI-a may be isolated by cooling the mixture formed after the addition of water, to a temperature of about 5° C. to about 0° C., followed by filtering and drying. Preferably, the mixture is cooled over a period of about 40 to about 50 minutes.

The invention further encompasses a process for preparing Rocuronium bromide of formula I

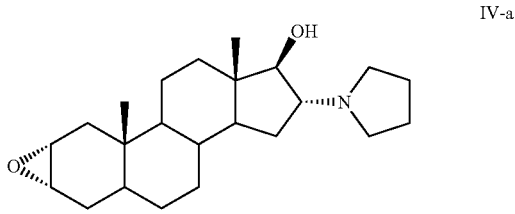

by preparing Compound VI with less than about 3% area by HPLC of Compound VI-a as described above, and converting it to Rocuronium bromide.

The invention also encompasses a process for preparing Compound IV:

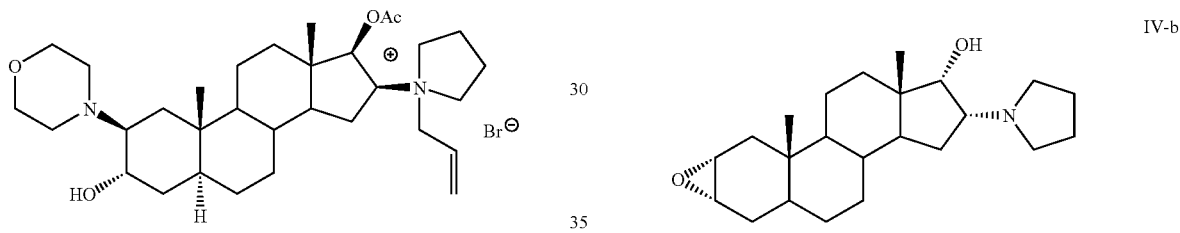

comprising forming a solution of Compound VI with less than about 3% of compound VI-a, and a water miscible organic solvent optionally combined with a water immiscible organic solvent; adding at least one reducing agent to the solution at a temperature of about −15° C. to about 10° C. to obtain a mixture; stirring the mixture at a temperature of about 20° C. to about 24° C.; and isolating Compound IV from the mixture having a purity of at least 85% area by HPLC, preferably at least 90% area by HPLC. Optionally, Compound IV can be obtained in a purity of above 97% area by HPLC by dissolving the isolated Compound IV in methanol, adding water to promote crystallization, and collecting the crystals.

As illustrated in comparative example 27 below, when the process for preparing compound IV disclosed in U.S. Pat. No. 4,894,369 is performed, two major more polar impurities are formed. These impurities were identified after the reduction of the carbonyl group, by NMR, MS and by XRD analysis, to be the isomers of the desired monoepoxide of formula IV. The isomer 2α,3α-epoxy-16α-(1-pyrrolidinyl)-17β-hydroxy-5α-androstane of formula IV-a (referred to as compound IV-a)

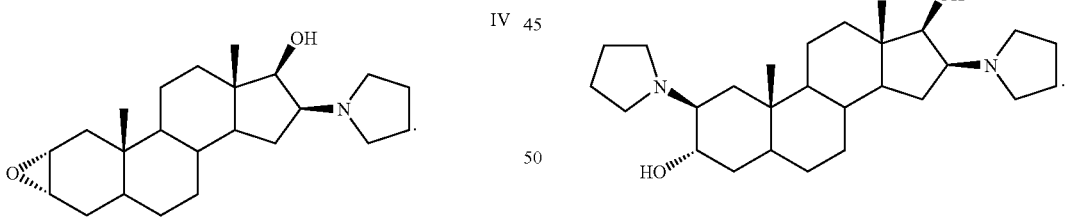

that is obtained in about 12% area by HPLC, and the second isomer 2α,3α-epoxy-16α-(1-pyrrolidinyl)-17α-hydroxy-5α-androstane of formula IV-b (referred to as compound IV-b)

that is obtained in about 5% area by HPLC. Moreover, impurity IV-c (dipyrrolidino analogue of the following formula) is obtained in no more than 4% area by HPLC.

Moreover, the process disclosed in U.S. Pat. No. 4,894,369, leads to the product in moderate yields of about 57% by weight. However, compound IV is obtained by the process the present invention in a much better yield, of about 80%.

Compound IV is obtained from the above process in purity of about 85% to about 100% area by HPLC, more preferably, of about 90% to about 100% area by HPLC, most preferably, of about 97% to about 100% area by HPLC.

Moreover, compound IV prepared by the above process, contains an impurity selected from a group consisting of: compound IV-a, compound IV-b, IV-c and mixtures thereof. Preferably, compound IV-a is present in an amount of less than about 2% area by HPLC, more preferably, of about 1% to about 2% area by HPLC. Preferably, compound IV-b is present in an amount less than about 1% area by HPLC. In addition, compound IV is obtained having less than about 2%, preferably less than about 0.5%, area by HPLC of compound IV-c of the following formula.

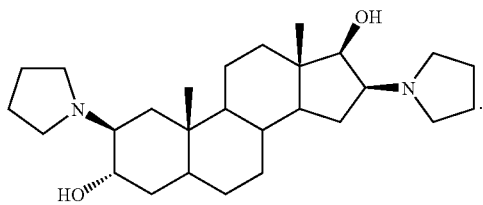

IV-c

Preferably, compound VI used as a starting material is with less than about 3% area by HPLC of Compound VI-a, thus the obtained compound IV contains less than about 2% area by HPLC, more preferably, of about 1% to about 2% area by HPLC of compound IV-a, less than about 1% area by HPLC of compound IV-b, and less than about 2%, preferably less than about 0.5% of compound VI-c.

Preferably, the water miscible organic solvent is at least one straight or branched $C_{1-5}$ alcohol. Preferably, the straight or branched $C_{1-5}$ alcohol is a $C_{1-3}$ alcohol. More preferably, the straight or branched $C_{1-3}$ alcohol is methanol, ethanol or isopropanol. The most preferred $C_{1-3}$ alcohol is methanol. When the water miscible organic solvent is present in combination with a water immiscible organic solvent, a preferred water miscible organic solvent is methanol and a preferred water immiscible organic solvent is methylene chloride.

Preferably, the reducing agent is added at a temperature of about 0° C. to about −5° C.

The reducing agent used in the reaction is any reducing agent capable of reducing the carbonyl. The reducing agent is preferably, a metal hydride complex, more preferably, an alkali metal hydride complex, most preferably, sodium borohydride, potassium borohydride, or sodium trimethoxy borohydride, and even most preferably, sodium borohydride.

Compound IV may be isolated by any method known to the skilled artisan. Such methods include, but are not limited to, concentration under vacuum and optionally addition of water to the organic phase.

Compound IV may optionally be purified by a process comprising: dissolving Compound IV in an organic solvent; extracting the solution at least once with a mineral acid; heating the solution to reflux to distill off about ⅔ of the solvent; adding water to the solution at a temperature of above about room temperature to form a suspension; cooling the suspension to induce precipitation of a solid; recovering the solid from the suspension; and drying the solid to obtain Compound IV.

The invention encompasses a process for preparing Roc of formula I by preparing compound IV having a purity of at least 90% area by HPLC as described above, preferably more than 95%, and converting it to Roc of formula I.

The invention further encompasses a process for preparing Compound VII

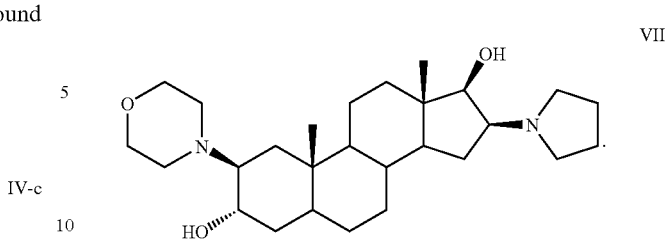

VII comprising forming a suspension of Compound IV, morpholine, and at least one acid catalyst; stirring the suspension at a temperature of about 100° C. to about reflux for about 24 hours to about 48 hours; and isolating Compound VII from the suspension.

The isolation of Compound VII as disclosed in U.S. Pat. No. 4,894,369, involves evaporation of morpholine, which is very inconvenient and time consuming. Moreover, the isolation of Compound VII further requires crystallization and recrystallization processes, thus reducing the yield and increasing the production cost. See '369 patent, col. 4, 1.47 to col. 5, 1.2 (examples 3 and 4). In contrast, crude compound VII of the present invention is obtained in high molar yields, preferably of about 82% to about 96%, by the above process while avoiding work-up steps. Moreover, compound VII obtained by the process of the invention has a purity of about 77% to about 98% area by HPLC, more preferably, of about 94% to about 98% area by HPLC, and thus can be used in the next stage without further purification.

Preferably the morpholine is in a form of an aqueous solution.

The acid catalyst should be a compound capable of increasing the rate of reaction. Typical acid catalysts include, but are not limited to, mineral acids, organic acids or Lewis acids. A preferred organic acid is p-toluene sulfonic acid, methane sulfonic acid, trichloroacetic acid, or trifluoroacetic acid. Preferably, the mineral acid is either sulfuric acid or hydrochloric acid. A preferred Lewis acid is $AlCl_3$, $ZnCl_2$, $BF_3$, $SnCl_4$, $TiCl_4$, $AgClO_4$, $Zn(OAc)_2$, or $FeCl_3$. A more preferred Lewis acid is either zinc acetate or ferric chloride. The most preferred catalyst is p-toluene sulfonic acid.

Preferably, the suspension is stirred at a temperature of about 100° C. to about 110° C.

Preferably, the suspension is stirred at a temperature of about 100° C. to about 110° C. to obtain a solution.

Preferably, the solution is maintained for 20 to about 50 hours, more preferably, under stirring.

Optionally, to increase the reaction rate, the suspension can be maintained under pressure, preferably the pressure of the solvent vapour. The pressure is preferably, of about 0.5 to about 1 $Kgf/cm^2$. When the suspension is maintained under pressure, the reaction temperature increases to about 113° C. to about 117° C.

Preferably, compound VII may be isolated by precipitating from a cold diluted aqueous basic solution and drying in a vacuum oven, thus avoiding the crystallization step disclosed in U.S. Pat. No. 4,894,369. More preferably, the basic solution is of an alkaline base selected from the group consisting of sodium carbonate, sodium bicarbonate, potassium carbonate, potassium bicarbonate, sodium hydroxide and potassium hydroxide. The most preferred base is sodium carbonate.

The process for the preparation of compound VII, more preferably, from compound IV, can be performed on an industrial scale.

The present invention also encompasses a process for preparing Roc of formula I by preparing compound VII as described above, and converting it to Roc of formula I. As illustrated in comparative example 26 below, repeating the procedure disclosed in U.S. Pat. No. 4,894,369, provides compound VIII in a purity of 81.56% area by HPLC, containing the starting diol, compound VII, in an amount of 5.16% area by HPLC and the diacetate impurity, compound IX, in an amount of 11.93% area by HPLC.

However, the process of the present invention applies the use of a small amount of a base and anhydride as the acetylating reagent and thus, leads chemoselectively to compound VIII in better yields and with a purity of about 90% to about 99% area by HPLC before purification. After purification by simple crystallization, the product is obtained in overall yield of about 70% and in purity of about 97% to above 99% area by HPLC, most preferably above 99%area by HPLC, without the need to purify by column chromatography.

The invention encompasses a process for the preparation of Compound VIII

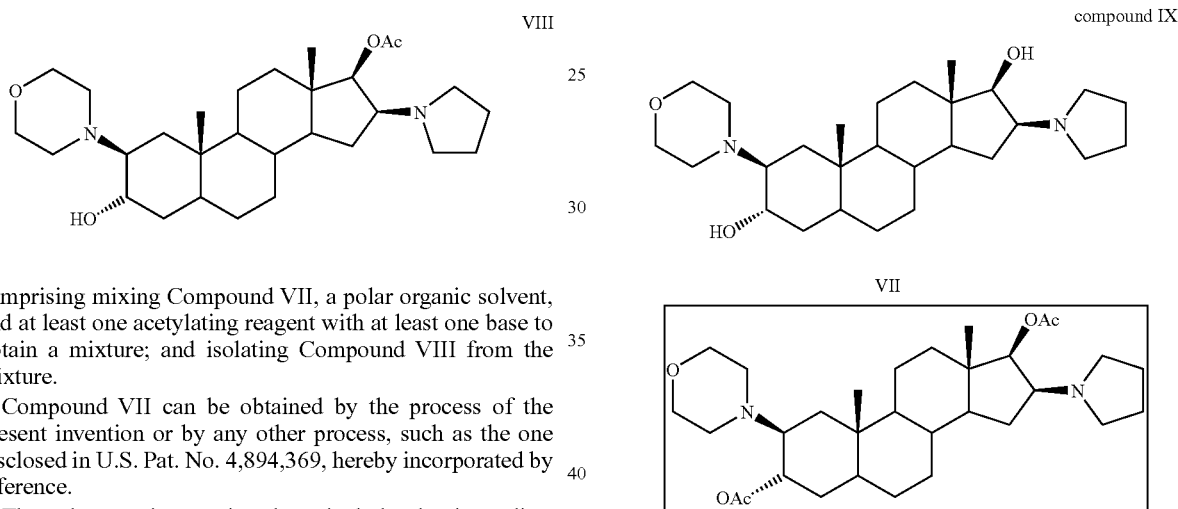

comprising mixing Compound VII, a polar organic solvent, and at least one acetylating reagent with at least one base to obtain a mixture; and isolating Compound VIII from the mixture.

Compound VII can be obtained by the process of the present invention or by any other process, such as the one disclosed in U.S. Pat. No. 4,894,369, hereby incorporated by reference.

The polar aprotic organic solvent includes, but is not limited to, ketones, esters, ethers, amides, nitromethane, or halogenated hydrocarbons. A preferred ketone is a $C_{3-6}$ ketone. A preferred $C_{3-6}$ ketone is either acetone or methylisobutylketone. Preferably, the ester is a $C_{4-6}$ ester. A preferred $C_{4-6}$ ester is either ethyl acetate or isobutyl acetate. A preferred ether is a $C_{3-4}$ cyclic ether, more preferably, tetrahydrofuran (THF). A preferred amide is a $C_{3-4}$ amide, more preferably, N,N-dimethylformamide. Preferably, the halogenated hydrocarbon is a $C_{1-2}$ halogenated hydrocarbon. A preferred $C_{1-2}$ halogenated hydrocarbon is either dichloromethane or dichloroethane. The more preferred solvent polar aprotic organic is dichloromethane.

The acetylating reagent includes, but is not limited to, acetyl halides, halogenated esters, anhydrides, or esters. A preferred acetyl halide is acetyl chloride. A preferred halogenated ester is either $AcOCH_2CCl_3$, or $AcOCH_2CF_3$. Preferably, the anhydride may be mixed anhydrides or acetic anhydride. Preferably, the ester is isopropenyl acetate. The more preferred acetylating reagent is acetyl chloride or acetic anhydride.

Typically, the base includes an organic bases or inorganic bases. Organic bases include, but are not limited to, aliphatic amines and aromatic amines. Preferably, the aliphatic amine is triethylamine, diethylisopropylamine, tri-n-propylamine or tributylamine. Preferably, the aromatic amine is 4-dimethylaminopyridine. Inorganic bases include, but are not limited to alkaline and aluminum bases. Preferably, the alkaline base is sodium carbonate or sodium bicarbonate. A preferred aluminum base aluminum oxide.

The more preferred base is triethyl amine, pyridine or sodium carbonate.

Preferably, the mixture is stirring the mixture at a temperature of about 0° C. to about 60° C., more preferably, at a temperature of about 20° C. to about 24° C. Preferably, the mixture is stirred for about 12 hours to about 48 hours, more preferably, the mixture is stirred for about 12 hours to about 22 hours.

Compound VIII may be isolated by any method known to the skilled artisan. Such methods include, but are not limited to, neutralizing the mixture by adding an aqueous basic solution, separating the organic and aqueous phase, washing the organic phase with water, filtering the organic phase, and concentrating the organic phase under vacuum.

The isolated compound VIII contains an impurity selected from a group consisting of: compound VII, and mixtures thereof. Preferably, compound VII is present in the crude compound VIII in an amount of no more than about 1.7% area by HPLC, more preferably, of about 0.2% to about 1.24% area by HPLC. Preferably, compound IX is present in an amount of no more than about 7%, more preferably, about 1% to about 5.2% area by HPLC.

Optionally, the isolated compound VIII may be purified by crystallization from a mixture of wet acetonitrile and dichloromethane, to yield compound VIII having a purity of about 90% to about 99.9% area by HPLC.

Preferably, the level of compound VII in compound VIII can be decreased significantly by the above crystallization process. Compound VIII obtained by the above crystallization process contains an impurity selected from a group consisting of: compound VII, compound IX and mixtures thereof. Preferably, compound VII is present in an amount of no more than 0.3% area by HPLC, more preferably, of about 0.1% to 0.3% area by HPLC. Preferably, compound IX is present in an amount of no more than 1% area by HPLC, more preferably, no more than about 0.5% area by HPLC.

Performing a second crystallization, as described above, leads to compound VIII that contains an impurity selected from a group consisting of: compound VII, compound IX and mixtures thereof. Preferably, compound VII is present in an amount of no more than 0.3% area by HPLC, more preferably, no more of about 0.2% area by HPLC. Preferably, compound IX is present in an amount of no more than 0.3% area by HPLC, more preferably, of about 0.1% to 0.3% area by HPLC.

Preferably, wet acetonitrile contains of about 1% to about 5% of water by volume, more preferably, of about 1% to about 1.25% of water by volume.

The process for the preparation of compound VIII, more preferably from compound VII, can be performed in an industrial scale.

The invention encompasses a process for the synthesis of rocuronium bromide (Compound I), wherein the amount of side products are minimized. Side products include compounds such as,

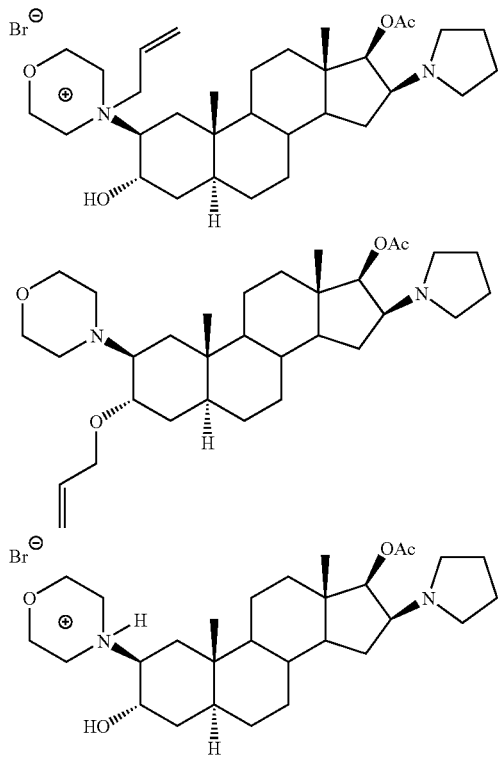

that are obtained when a large excess of allyl bromide is used.

The process of the invention has a molar yield of about 95% of rocuronium bromide, which is obtained by precipitation from a mixture of dichloromethane and diethylether. The precipitation avoids complex or time consuming purification steps.

The process for preparing rocuronium bromide comprises combining Compound VIII, a polar aprotic organic solvent, allyl bromide, and at least one inorganic base to obtain a mixture; and isolating rocuronium bromide.

Roc obtained by the above process, has a purity of at least about 94% area by HPLC, preferably of about 99% to about 100% area by HPLC.

The polar aprotic organic solvent includes, but is not limited to, halogenated hydrocarbons, esters, or ketones. A preferred halogenated hydrocarbon is a $C_{1-2}$ halogenated hydrocarbon, more preferably, dichloromethane. A preferred ester is a $C_{3-4}$ ester, more preferably, ethylacetate. Preferably, the ketone is a $C_{3-4}$ ketone, more preferably, acetone. The more preferred polar aprotic organic solvent is dichloromethane.

The amount of allyl bromide should be sufficient to yield the desired product without forming large amounts of the undesired side products. Preferably, the allyl bromide is present in an amount of about 1.3 to about 3 mole equivalents per mole of compound VIII, more preferably, in an amount of about 2 mole equivalents per mole of compound VIII, instead of 8 mole equivalents as used in the process disclosed in U.S. Pat. No. 4,894,369.

Preferably, the mixture of compound VIII, polar aprotic organic solvent and the allyl bromide have low water content, more preferably, of less than about 0.1% water content by Karl Fischer, even more preferably, less than 0.05% water content, and most preferably, less than about 0.03% water content.

The presence of the inorganic base inhibits competing reaction providing undesired side products, such as

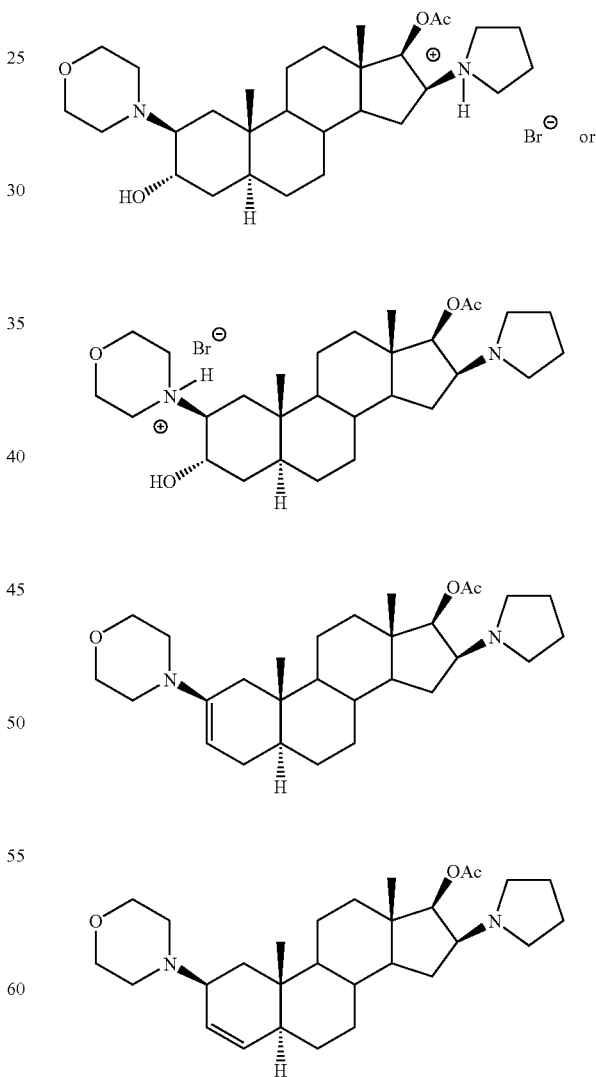

Additional side products include:

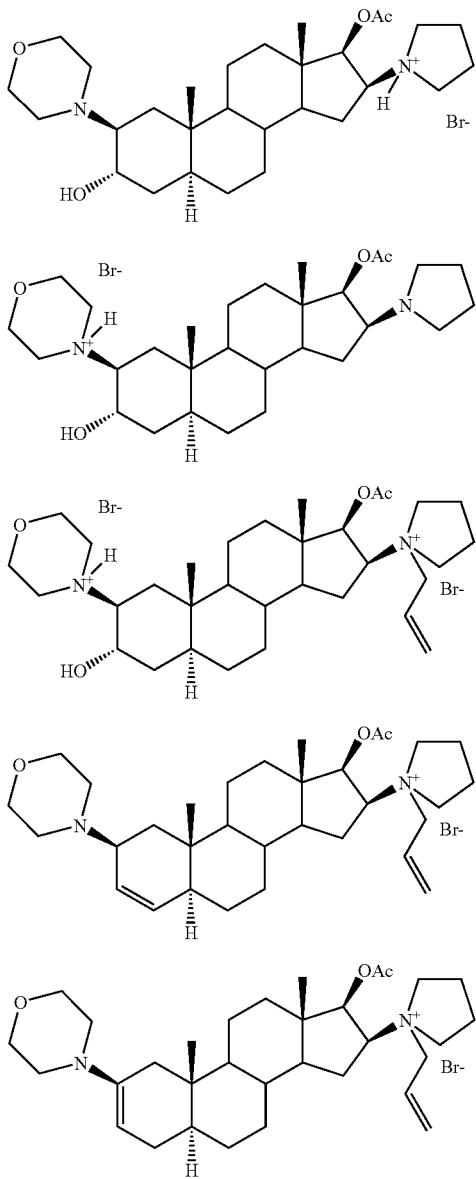

The presence of inorganic bases allows faster conversion under milder conditions, slowing the rate of competing reactions which produce side-products such as structures A-E (see scheme above). Structure C is the protonated form of Roc-1 and its presence affects the potentiometric assay.

Optionally, compound VII, allyl bromide and the polar aprotic organic solvent can be treated separately with an inorganic base, prior to combining them. The inorganic base includes, but is not limited to alkaline and aluminum bases. More preferably, the alkaline base is sodium carbonate, sodium bicarbonate or potassium carbonate. A more preferred aluminum base is aluminum oxide. The most preferred inorganic base is sodium carbonate.

Preferably, the mixture is stirred at a temperature of about 15° C. to about 40° C., more preferably, at a temperature of about 35° C. to about 40° C.

Preferably, the mixture is maintained for about 20 hours to about 24 hours, more preferably, for about 22 hours to about 24 hours.

Crude rocuronium bromide may be isolated by any method known to the skilled artisan. Such methods include, but are not limited to, concentrating the resultant reaction mixture, dissolving the residue with dichloromethane and filtering off salts that are used in the reaction, such as sodium carbonate.

Crude Roc of formula I obtained by the above process, may be further purified by a process comprising dissolving the crude rocuronium bromide in at least one polar aprotic organic solvent to form a solution; adding a decolorizing agent optionally combined with a base to the solution to form a first suspension; filtering the first suspension; adding the resulting filtrate to an anti-solvent; stirring vigorously to obtain a second suspension; recovering wet solid Rocuronium bromide from the second suspension; and drying the wet Rocuronium bromide at a temperature of no more than about 35° C.

Preferably, prior to using the decolorizing agent, excess allyl bromide is removed from crude Rocuronium bromide. The excess allyl bromide may be removed from the crude Rocuronium bromide by dissolving the rocuronium bromide in at least one polar aprotic organic solvent, and removing the solvent, preferably by evaporation, to obtain an oily residue. Dissolution and removal of the solvent can be repeated as many times required to remove excess of allyl bromide.

The polar aprotic organic solvent includes, but is not limited to, halogenated hydrocarbons, esters, or ketones. Preferably, the halogenated hydrocarbon is dichloromethane. A preferred ester is ethyl acetate. Preferably, the ketone is acetone. More preferably, the polar aprotic organic solvent is dichloromethane.

The decolorizing agent includes, but is not limited to, aluminum oxide, activated charcoal, or silica gel. When the decolorizing agent is not basic then a base may be used in combination with the decolorizing agent. Preferably, the decolorizing agent is aluminum oxide. Preferably, the base is sodium bicarbonate.

The mixing of the filtrate with the anti-solvent is performed while stirring vigorously. The conditions for stirring "vigorously" depend on the size of the reaction vessel. On a small scale, e.g, 100 ml flask, 800-1000 rpm corresponds to stirring "vigorously." On a larger scale, e.g., a 1000 L flask, an impeller/stirrer at 250 rpm in presence of baffles can be considered stirring "vigorously." Stirring vigorously allows one to obtain a product which can be dried to a low residual solvent content.

Preferably, the anti-solvent is selected from a group consisting of: ether, ester and aromatic hydrocarbon and mixtures thereof. Preferably, the preferred ether is either diethyl ether or diisopropyl ether. Preferably, the ester is ethyl acetate. A preferred aromatic hydrocarbon is toluene. Preferably, the solvent in the filtrate is dichloromethane and the anti-solvent is diethyl ether. Typically, when the solvent is dichloromethane and anti-solvent is diethyl ether, the reaction yields about 112% to 118% w/w of rocuronium bromide.

Preferably, rocuronium bromide is dried under vacuum for at least 5 days at a temperature of no more than about 35° C.

The process for the preparation of Roc of formula I, more preferably from compound VIII, can be performed in an industrial scale.

The present also invention encompasses a process for the preparation of the quaternary ammonium salt, Roc, of formula I

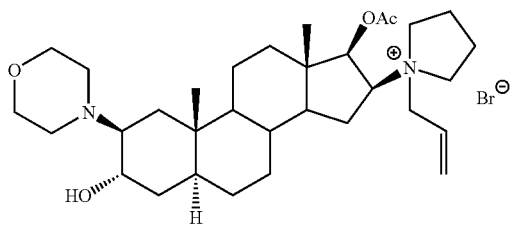

I comprising combining a starting Compound VI containing about 10% to about 40% area by HPLC of Compound VI-a with a water miscible organic solvent to obtain a suspension; stirring the suspension at a temperature of about 60° C. to about 80° C. to obtain a mixture; adding water to the mixture; isolating Compound VI from the mixture, wherein the isolated Compound VI is with less than about 3% area by HPLC of Compound VI-a; forming a solution of Compound VI with less than about 3% of compound VI-a, and a water miscible organic solvent optionally combined with a water immiscible organic solvent; adding at least one reducing agent to the solution at a temperature of about −15° C. to about 10° C. to obtain a mixture; stirring the mixture at a temperature of about 20° C. to about 24° C.; isolating Compound IV from the mixture having a purity of at least 85% area by HPLC; forming a suspension of Compound IV, morpholine, and at least one acid catalyst; stirring the suspension at a temperature of about 100° C. to about reflux for about 24 hours to about 48 hours; isolating Compound VII from the suspension; combining Compound VII, a polar organic solvent, and at least one acetylating reagent with at least one base to obtain a mixture; isolating Compound VIII from the mixture; combining Compound VII, a polar aprotic organic solvent, allyl bromide, and at least one inorganic base to obtain a mixture; and isolating rocuronium bromide.

While the present invention is described with respect to particular examples and preferred embodiments, it is understood that the present invention is not limited to these examples and embodiments. The present invention, as claimed, therefore includes variations from the particular examples and preferred embodiments described herein, as will be apparent to one of skill in the art.

EXAMPLES

X-ray Diffraction Analysis of 2α,3α-epoxy-16β-(1-pyrrolidinyl)-5α-androstan-17-one, Compound VI Powder X-ray diffraction (PXRD) was performed on an ARL X-Ray powder diffractometer model X'TRA-030, θ-θ goniometer, Cu-tube, solid state detector with Peltier cooling. The sample holder was a round standard aluminium sample holder with round zero background quartz plate with a cavity of 25 (diameter)×0.5 mm (depth). Scanning parameters: Range: 2-40 degrees two-theta; Scan mode: continuous scan; and Scan rate: 3 deg/min.

Differential Scanning Calorimetry (DSC)

The differential scanning calorimetry was performed on a DSC 822$^e$/700, Mettler Toledo with a sample weight: 3-5 mg. The heating rate: 10° C./min., and the number of holes of the crucible was 3. The $N_2$ stream: flow rate was 40 ml/min and the scan range was 30-250° C.

Thermal Gravimetric Analysis (TGA)

The thermal gravimetric analysis was performed on a TGA/SDTA 851$^e$, Mettler Toledo and the sample weight was 7-15 mg. The heating rate was 10° C./min., and the $N_2$ stream flow rate was 50 ml/min. The scan range was 25-250° C.

Example 1

Preparation of the Mixture of 2α,3α-epoxy-16β-(1-pyrrolidinyl)-5α-androstan-17-one, Compound VI, and 2α,3α-epoxy-16α-(1-pyrrolidinyl)-5α-androstan-17-one, Compound VI-a To a solution of 2α,3α,16α,17α-bisepoxy-5α-androstan-17β-ol acetate III (50 g, 144.32 mmol) in methanol (500 mL) was added a 4 N solution of sodium hydroxide (40 mL, 9.525, 158.75 mmol) at 20-24° C. and under nitrogen atmosphere. The mixture was heated to reflux (60-65° C.) for 30 min, followed by cooling to 40° C. and addition of pyrrolidine (24 mL, 288.64 mmol). The reaction mixture was heated to reflux (60-65° C.) for 30-45 min, followed by cooling to room temperature and then ice-water (500 mL) was added, to obtain a suspension. The suspension was stirred at 5° C. for 30 min and then the solid was filtered off and washed with cold water (2×200 mL). The wet solid was dried under vacuum to give 47 g of Compound VI as a pale yellow powder having a ratio of VI-a to VI of 18:82.

Example 2

Equilibration Process to Obtain 2α,3α-epoxy-16β-(1-pyrrolidinyl)-5α-androstan-17-one, Compound VI The dried compound of Example 1 (47 g) was suspended in methanol (235 mL) and refluxed (60-65° C.) between 20-30 min. Water was added (715 mL) over a period of 20 min. and the resulting mixture was heated at 65-70° C. during 30 min. The formed suspension was cooled at 0-5° C. in a period of 30-40 min and the suspension was further stirred at this temperature for 20 min. The suspension was filtered and washed with water (188 mL). The wet solid was dried under vacuum to give 43 g (120.26 mmol, 83% yield, purity of 93% by HPLC, having a melting point of 146° C.) of Compound VI as a white solid, having a ratio of VI-a to VI of 1.8:98.2. $[\alpha]_D^{20}$+ 101.1 (c=1.0 in $CHCl_3$).

Example 3

Preparation of 2α,3α-epoxy-16β-(1-pyrrolidinyl)-5α-androstan-17β-ol, Compound IV A suspension of 1 g (2.8 mmol) of Compound VI in of methanol (20 mL) was cooled to −10° C., and then sodium borohydride (200 mg, 5.04 mmol) was added carefully in portions, under a nitrogen atmosphere. The resulting heterogeneous reaction mixture was allowed to reach 20-24° C. and stirred for at least 3 h. The reaction mixture was diluted with $CH_2Cl_2$ and then purified water was added at 20-22° C. The solution was stirred for 10 min. and then the phases were separated. The organic phase was washed with purified water and the solution was concentrated under vacuum to give the desired crude Compound IV. The product was dried in a vacuum oven at 40° C. for at least 16 h to give 1 g ( 0.00278 mole) of a white solid (99.3% yield) containing the product IV 98.5% and the isomer IV-a 1.1% area by HPLC. M.P. 171° C.; [α]D20+34.0 (c=1.0 in $CHCl_3$). The structure was confirmed by spectroscopic analysis.

Characterization data of: 2α,3α-epoxy-16α-pyrrolidin-1-yl)-17β-hydroxy-5α-androstan of Compound IV-a.

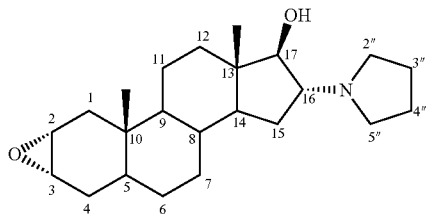

C₂₃H₃₇NO₂
Exact Mass 359.28
Mol. Wt.: 359.55
C, 76.83; H, 10.37; N, 3.90; O, 8.90

¹H NMR (300 MHz, CDCl₃):

| δ (ppm) | Multiplicity | (H) | $J_{H-H}$ (Hz) | Assignment |
|---|---|---|---|---|
| 3.60 | doublet | (1) | 6.6 | H-17α |
| 3.15-3.09 | multiplet | (2) | | H-2β, H-3β |
| 2.75-2.66 | multiplet | (5) | | H-16β, H-2", H-5" |
| 1.94-0.62 | multiplets | (23) | | All other aliphatic hydrogens |
| 0.77 | singlet | (3) | | CH₃ |
| 0.76 | singlet | (3) | | CH₃ |

¹³C NMR (300 MHz, CDCl₃):

| δ (ppm) | Assignment |
|---|---|
| 85.0 | CH, C-17 |
| 69.9 | CH, C-16 |
| 53.6 | CH, C-2 |
| 52.3 | CH, C-3 |
| 52.2 | CH₂ |
| 50.9 | CH |
| 48.8 | CH |
| 43.5 | C |
| 38.1 | CH₂ |
| 36.5 | CH₂ |
| 36.2 | CH |
| 35.3 | CH |
| 33.7 | C |
| 31.0 | CH₂ |
| 29.0 | CH₂ |
| 28.7 | CH₂ |
| 28.2 | CH₂ |
| 23.2 | CH₂ |
| 20.1 | CH₂ |
| 12.9 | CH₃ |
| 12.2 | CH₃ |

| Mass Spectrometry | 359 m/z: (M) |
|---|---|
| IR | 3462 cm⁻¹ (O—H) |
| | 1133 cm⁻¹ (C—N) |

Characterization data of: 2α,3α-epoxy-16α-(pyrrolidin-1-yl)-17α-hydroxyl-5α-androstan of Compound IV-b

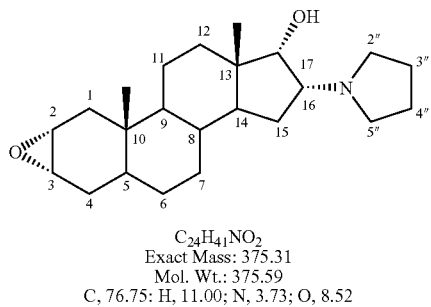

C₂₄H₄₁NO₂
Exact Mass: 375.31
Mol. Wt.: 375.59
C, 76.75; H, 11.00; N, 3.73; O, 8.52

¹H NMR (300 MHz, CDCl₃):

| δ (ppm) | Multiplicity | (H) | $J_{H-H}$ (Hz) | Assignment |
|---|---|---|---|---|
| 3.48 | doublet | (1) | 4.8 | H-17β |
| 3.15-3.09 | multiplet | (2) | | H-2β, H-3β |
| 2.81 | multiplet | (1) | | H-16β |
| 2.66 | multiplet | (2) | | H-2" |
| 2.54 | multiplet | (2) | | H-5" |
| 1.95-0.62 | multiplet | (23) | | All other aliphatic hydrogens |
| 0.76 | singlet | (3) | | CH₃ |
| 0.68 | multiplet | (3) | | CH₃ |

¹³C NMR (300 MHz, CDCl₃):

| δ (ppm) | Assignment |
|---|---|
| 78.3 | CH, C-17 |
| 67.0 | CH, C-16 |
| 53.4 | CH, C-2 |
| 53.3 | CH₂ |
| 52.3 | CH, C-3 |
| 51.0 | CH |
| 47.4 | CH |
| 45.0 | C |
| 38.2 | CH₂ |
| 36.2 | CH |
| 35.7 | CH |
| 33.7 | C |
| 31.9 | CH₂ |
| 31.0 | CH₂ |
| 29.5 | CH₂ |
| 29.0 | CH₂ |
| 28.4 | CH₂ |
| 23.3 | CH₂ |
| 19.9 | CH₂ |
| 16.6 | CH₂ |
| 12.9 | CH₃ |

| Mass Spectrometry | 360 m/z: (M⁺) |
|---|---|
| IR | 3413 cm⁻¹ (O—H) |
| | 1225 cm⁻¹ (C—N) |

Example 4

Preparation of 2α,3α-epoxy-16,β-(1-pyrrolidinyl)-5α-androstan-17β-ol Compound IV The title compound was prepared as a solid following the procedure of Example 3 and using ethanol as solvent; m.p. 154.5° C.; $[\alpha]_D^{20}$+29.4° (c=1.0 in CHCl$_3$).

Example 5

Preparation of 2α,3α-epoxy-16β-(1-pyrrolidinyl)-5α-androstan-17β-ol, Compound IV The title compound was prepared as a solid following the procedure of Example 3 and using isopropanol as solvent; m.p. 158° C.; $[\alpha]_D^{20}$+33.6° (c=1.0 in CHCl$_3$).

Example 6

Preparation of 2β-(4-morpholinyl)-16β-(1-pyrrolidinyl)-5α-androstan-3α,17β-diol, Compound VII A suspension of 2α,3α-epoxy-16β-(1-pyrrolidinyl)-5α-androstan-17β-ol (1.80 Kg, 5.006 mol) in a mixture of morpholine (11.44 L) and purified water (1.144 L) was prepared at 20-24° C. and under N$_2$ atmosphere. To the suspension was added p-toluenesulphonic acid (1.24 Kg, 6.508 mol) at 20-24° C. and under N$_2$ atmosphere. The suspension was stirred in the darkness and heated to reflux (100-110° C.) for 40 h. After 40 h the reaction mixture was cooled to 20-24° C., and poured into a second vessel maintained at about 4° C. containing a 2% s solution of sodium carbonate (128 L), while stirred vigorously. The resulting suspension was stirred for 1 hour at about 4° C. The obtained solid was filtered off under vacuum, washed with cold purified water (100 L), and dried in a vacuum oven at about 40° C. for at least 48 hours, to give 2.07 Kg (4.49 mol) of a white solid. (89.7% molar yield and purity of 94.12% area by HPLC) m.p. 225° C.; [α]D20+82.00 (c=1.02 in CHCl$_3$). The product could be used in the next stage without further purification.

The obtained product was further crystallized from methanol and then was subjected to single crystal X-ray crystallography analysis that confirmed the stereochemistry of the product.

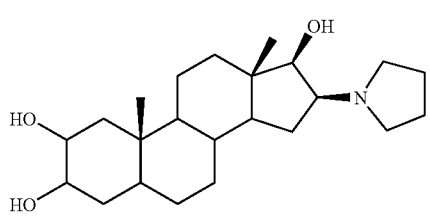

0.42% area by HPLC

Unknown impurity 5.16 area by HPLC. Unidentified impurities 0.29% area by HPLC.

Example 7

Preparation of 2β-(4-morpholinyl)-16β-(1-pyrrolidinyl)-5α-androstan-3α,17β-diol, Compound VII The title compound was prepared as a solid following the procedure of Example 6 and using methanesulphonic acid as catalyst; m.p. 230° C.

Example 8

Preparation of 2β-(4-morpholinyl)-16β-(1-pyrrolidinyl)-5α-androstan-3α,17β-diol, Compound VII The title compound was prepared as a solid following the procedure of Example 6 and using sulphuric acid as catalyst; m.p. 230° C.; $[\alpha]_D^{20}$+83.8° (c=1.02 in CHCl$_3$). The purity of the crude product by HPLC is 97.36% area. The crude contained the following impurities:

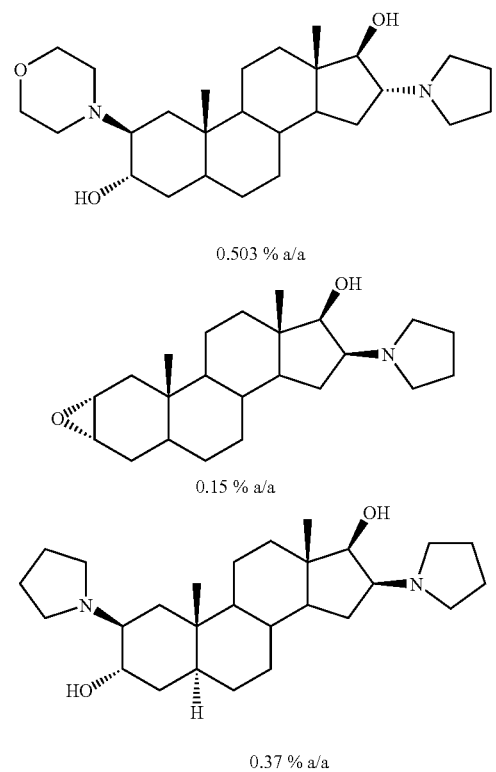

0.503 % a/a 0.15 % a/a 0.37 % a/a

Example 9

Preparation of 2β-(4-morpholinyl)-16β-(1-pyrrolidinyl)-5α-androstan-3α,17β-diol, Compound VII The title compound was prepared as a solid following the procedure of Example 6 and using hydrochloric acid as catalyst; m.p. 226° C.; $[\alpha]_D^{20}$+81.3° (c=1.02 in CHCl$_3$). The purity of the crude product by HPLC is 94.23% area. The crude contained the following impurities:

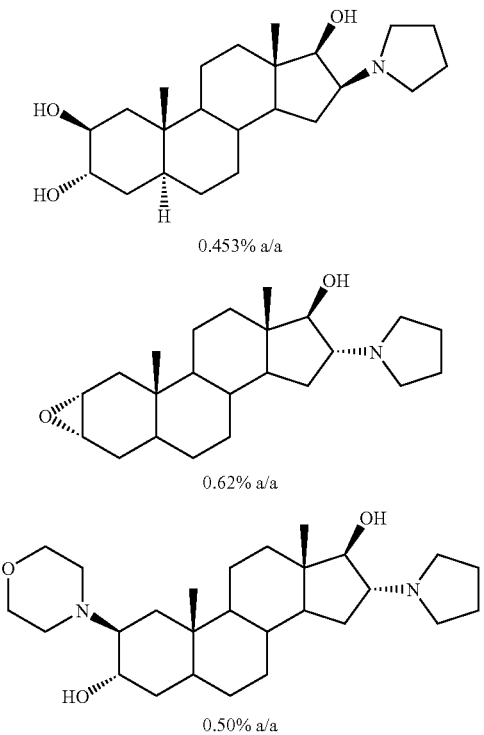

0.453% a/a 0.62% a/a 0.50% a/a

Example 10

Preparation of 2β-(4-morpholinyl)-16β-(1-pyrrolidinyl)-5α-androstan-3α,17β-diol, Compound VII The title compound was prepared as a solid following the procedure of Example 6 and using zinc acetate as catalyst; m.p. 218° C. The purity of the crude product by HPLC is 77.42% area. The crude contained the following impurities:

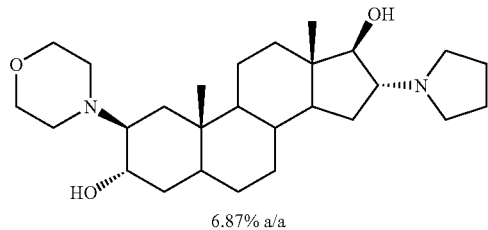

6.87% a/a

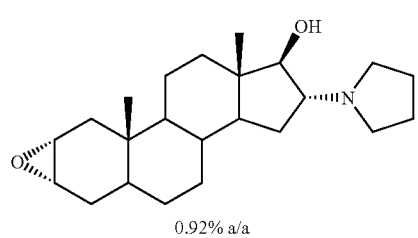

0.92% a/a

-continued

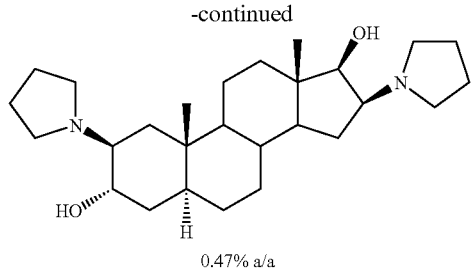

0.47% a/a and 0.82% area by HPLC of the starting material.

Example 11

Preparation of 2β-(4-morpholinyl)-16β-(1-pyrrolidinyl)-5α-androstan-3α,17β-diol, Compound VII The title compound was prepared as a solid following the procedure of Example 6 and using ferric chloride as catalyst; m.p. 216° C. The purity of the crude product by HPLC is 89.0% area. The crude contained the following impurities:

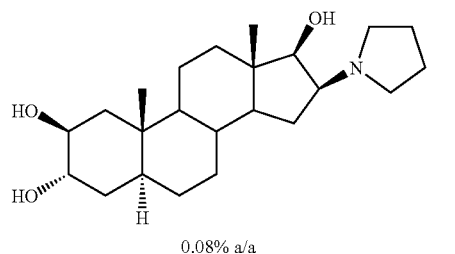

0.08% a/a

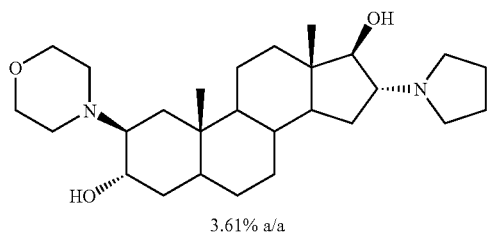

3.61% a/a

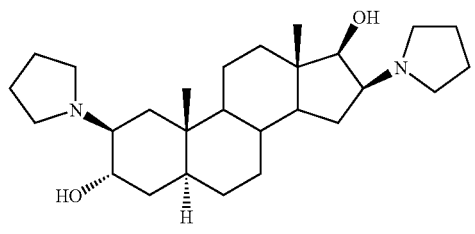

0.97% a/a and 0.76% area by HPLC of the starting material.

Example 12

Preparation of 2β-(4-morpholinyl)-16β-(1-pyrrolidinyl)-5α-androstan-3α,17β-diol, Compound VII The title compound was prepared as a solid following the procedure of Example 6 and using the standard conditions and NaOH during the work up; m.p. 229° C.; $[\alpha]_D^{20}$+83.5° (c=1.02 in $CHCl_3$). The purity of the crude product by HPLC is 97.17% area. The crude contained the following impurities:

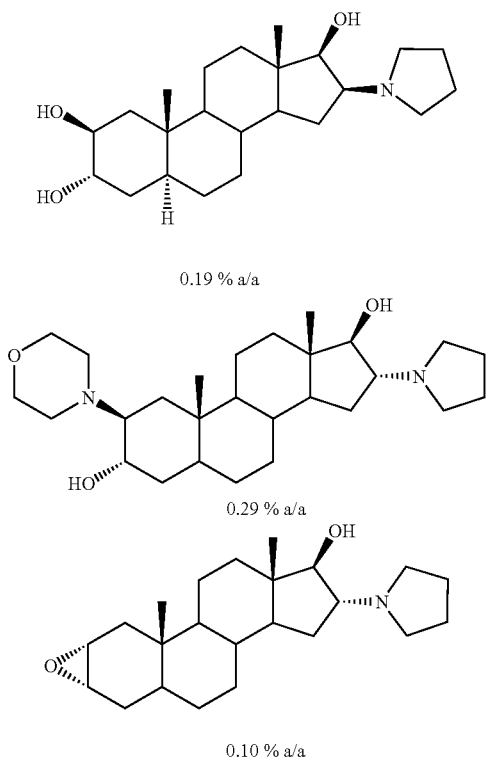

0.19 % a/a 0.29 % a/a 0.10 % a/a

Example 13

Preparation of 2β-(4-morpholinyl)-16β-(1-pyrrolidinyl)-5α-androstan-3α,17β-diol, Compound VII The title compound was prepared as a solid following the procedure of Example 6 and using the standard conditions without catalyst; m.p. 225° C.; [α]$_D^{20}$+81.3° (c=1.02 in CHCl$_3$). The purity of the crude product by HPLC is 94.45% area. The crude contained the following impurities:

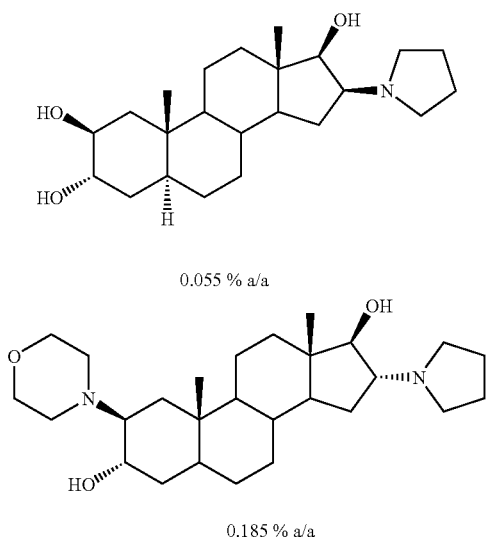

0.055 % a/a 0.185 % a/a

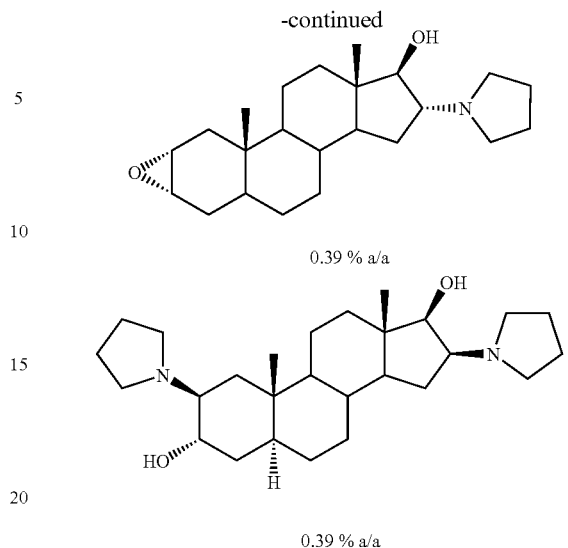

0.39 % a/a 0.39 % a/a and 1.01% area by HPLC of the starting material.

Example 14

Preparation of 2β-(4-morpholinyl)-16β-(1-pyrrolidinyl)-5α-androstan-3α,17β-diol 17-acetate, Compound VIII To a suspension of 2β-(4-morpholinyl)-16β-(1-pyrrolidinyl)-5α-androstan-3α,17β-diol (2.067 Kg, 4.628 mol) in dichloromethane (103.35 L) at 20-22° C., was added triethylamine (1.935 L, 13.883 mol) under N$_2$ atmosphere. The mixture was stirred until complete dissolution. Acetic anhydride (0.873 L, 9.255 mol) was charged slowly under continuous stirring and then the resulting reaction mixture was stirred for 22 h at a temperature of 20-22° C. A 5% Na$_2$CO$_3$ solution (41.34 L) was then added and the mixture was stirred for 5-10 min. The phases were separated and the organic phase was washed with water (2×41 L) at 15° C., dried with anhydrous Na$_2$SO$_4$ (10 Kg), and filtered under vacuum to remove salts, which were rinsed with dichloromethane (10 L). The solvent was removed under vacuum at a temperature lower than 20° C. until a final volume of 12 L was obtained. To the concentrated stirred solution at a maximum temperature of 20° C. was added wet acetonitrile (40 L), followed by concentrating under vacuum at a temperature lower than 15° C., to a total volume of 40 L of a suspension. The resulting suspension was cooled to 0-5° C., stirred for 1 h, filtered off under vacuum and washed with acetonitrile (3 L). The desired wet product was dissolved in dichloromethane (9.5 L) at 20-22° C., followed by addition of acetonitrile (38 L). The volume was reduced under vacuum at a temperature lower than 15° C. to a total volume of 39 L to give a suspension. The resulting suspension was cooled to 0-5° C. and stirred for 1 h. The obtained solid was filtered off under vacuum and the product was washed with acetonitrile (3 L). The pure product was dried in a vacuum oven at 40° C. for at least 15 h to give 1.51 Kg of a white solid. (68.8% molar yield and a purity of 99.9% by HPLC); M.P. 160° C.; [α]$_D^{20}$+55.5 (c=1.0 in CHCl$_3$).

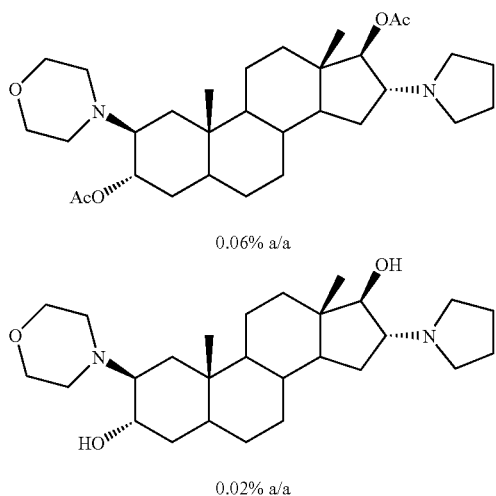

0.06% a/a 0.02% a/a

Example 15

Preparation of 2β-(4-morpholinyl)-16β-(1-pyrrolidinyl)-5α-androstan-3α,17β-diol 17-acetate, Compound VIII The title compound was prepared as a solid following the procedure of Example 14 and using acetyl chloride and triethylamine; m.p. 155° C.; $[\alpha]_D^{20}$+54.3 (c=1.0 in CHCl$_3$). The purity of the purified product is 97.48% area by HPLC containing the impurities: VII 1.24% area by HPLC and IX 1.05% area by HPLC.

Example 16

Preparation of 2β-(4-morpholinyl)-16β-(1-pyrrolidinyl)-5α-androstan-3α,17β-diol 17-acetate, Compound VIII The title compound was prepared as a solid following the procedure of Example 14 and using acetic anhydride and pyridine; m.p. 147.5° C.; $[\alpha]_D^{20}$+50.7 (c=1.0 in CHCl$_3$). The purity of the purified product is 93.92% area by HPLC containing the impurities: VII 0.88% area by HPLC and IX 5.19% area by HPLC.

Example 17

Preparation of 2β-(4-morpholinyl)-16β-(1-pyrrolidinyl)-5α-androstan-3α,17β-diol 17-acetate, Compound VIII The title compound was prepared as a solid following the procedure of Example 14 and using acetic anhydride and sodium carbonate; m.p. 153.5° C.; $[\alpha]_D^{20}$+50.9 (c=1.0 in CHCl$_3$). The purity of the purified product is 97.11% area by HPLC containing the impurities: VII 0.23% area by HPLC and IX 2.64% area by HPLC.

Example 18

Preparation of 2β-(4-morpholinyl)-16β-(1-pyrrolidinyl)-5α-androstan-3α,17β-diol 17-acetate, Compound VIII The procedure of example 13 was repeated using ethyl acetate as solvent. The obtained residue, as determined by HPLC, was a mixture of 25.37% of the desired Compound VIII, 4.4% of Compound IX and 49.26% of Compound VII.

Example 19

Preparation of 2β-(4-morpholinyl)-16β-(1-pyrrolidinyl)-5α-androstan-3α,17β-diol 17-acetate, Compound VIII The procedure of example 13 was repeated using isobutyl acetate as solvent. The obtained residue, as determined by HPLC, was a mixture of 23.74% of the desired Compound VIII, 11.52% of Compound IX and 17.34% of Compound VII.

Example 20

Preparation of 2β-(4-morpholinyl)-16β-(1-pyrrolidinyl)-5α-androstan-3α,17β-diol 17-acetate, Compound VIII The procedure of example 13 was repeated using methylisobutylketone as solvent. The obtained residue, as determined by HPLC, was a mixture of 35.0% of the desired Compound VIII, 6.9% of Compound IX and 17.0% of Compound VII.

Example 21

Preparation of 2β-(4-morpholinyl)-16β-(1-pyrrolidinyl)-5α-androstan-3α,17β-diol 17-acetate, Compound VIII A. The procedure of example 13 was repeated using dichloromethane as solvent and 0.1% w/w of water added in purpose. After a reaction time of 22 h, the obtained residue was a mixture of 90.54% of the desired Compound VIII, 3.70% of Compound IX and 3.99% of Compound VII as determined by HPLC.

B. The procedure of example 13 was repeated using dichloromethane as solvent and 0.5% w/w of water added in purpose. After a reaction time of 22 h, the obtained residue was a mixture of 87.41% of the desired Compound VIII, 2.26% of Compound IX and 8.79% of Compound VII as determined by HPLC.

The results are summarized in the following tables:

TABLE 1

| HPLC after 22 h reaction time | | | | |
|---|---|---|---|---|
| Water content [%] | | Area % | | |
| Theoretical | K.F. | VII | VIII | IX |
| 0 | 0.015 | 1.35 | 92.61 | 4.22 |
| 0.1 | 0.081 | 3.99 | 90.54 | 3.70 |
| 0.5 | 0.100 | 8.79 | 87.41 | 2.26 |
| 1.0 | 0.103 | 7.77 | 88.79 | 1.90 |

TABLE 2

| Water content [%] | | HPLC after 41 h reaction time | | |
|---|---|---|---|---|
| | | Area % | | |
| Theoretical | K.F. | VII | VIII | IX |
| 0.1 | 0.081 | 1.52 | 89.10 | 5.95 |
| 0.5 | 0.100 | 8.61 | 85.33 | 2.68 |
| 1.0 | 0.103 | 7.95 | 86.64 | 2.26 |

Example 22

Preparation of 2β-(4-morpholinyl)-16β-(1-pyrrolidinyl)-5α-androstan-3α,17β-diol 17-acetate, Compound VIII The procedure of example 16 was repeated using dichloromethane as solvent and 1% w/w of water added in purpose. After a reaction time of 22 h, the obtained residue was a mixture of 88.8% of the desired Compound VIII, 1.90% of Compound IX and 7.77% of Compound VI as determine by HPLC.

Example 23

Preparation of 1-[17β-acetyloxy-3α-hydroxy-2(4-morpholinyl)-5α-androstan-16β-yl]-1(2-propenyl) pyrrolidinium bromide, Compound I A solution of 2β-(4-morpholinyl)-16β-(1-pyrrolidinyl)-5α-androstan-3α,17β-diol 17-acetate (10 g, 0.02 mol) in dichloromethane (150 ml) was prepared at 20-22° C. under $N_2$ atmosphere. Then, 75 mL of were distilled at normal pressure. At the same time, a solution of allyl bromide (3.5 mL, 0.04 mol) in dichloromethane (25 ml) was prepared and mixed with sodium carbonate (5.2 g, 0.04 mol), followed by stirring for 30 minutes at room temperature. The suspension was filtered off through a 0.45 μm filter and added to the solution of 2β-(4-morpholinyl)-16β-(1-pyrrolidinyl)-5α-androstan-3α,17β-diol 17-acetate (10 g, 0.02 mol) in dichloromethane. The reaction was poured in to an amber Schott flask, purged, sealed and stirred for 22 hours at 40° C. The mixture was then cooled to room temperature and concentrated under vacuum keeping the temperature below 20° C. Dichloromethane (50 mL) was added to the flask and then concentrated under vacuum keeping the temperature below 20° C.; this procedure was repeated twice. The residue was dissolved at room temperature and nitrogen atmosphere in dichloromethane (111 mL), filtered through a 0.45 μm membrane and slowly added to diethyl ether (745 mL) with continuous stirring.

The resulting suspension was stirred for 30 minutes and filtered under nitrogen atmosphere. The solid obtained was dried at 35° C. for 60 hours to give 11.8 g (118% w/w, 94.58% mol/mol, purity of 99.4% by HPLC) containing Impurity A 0.1%; Impurity B 0.1% area by HPLC; and Impurity E 0.1% area by HPLC) of an off-white solid. m.p 209° C.; $[\alpha]_D^{20}$+ 29.8° (c=1.0 in $CHCl_3$).

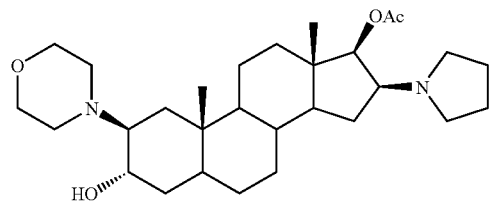

Impurity A

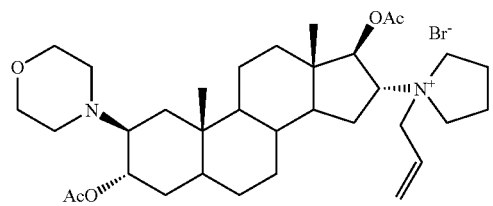

Impurity B

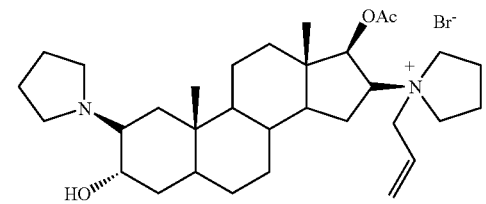

Impurity E

Example 24

Preparation of 1-[17β-acetyloxy-3α-hydroxy-2(4-morpholinyl)-5α-androstan-16β-yl]-1(2-propenyl) pyrrolidinium bromide, Compound I The title compound was prepared as a solid following the procedure of Example 14 and using acetone as reaction solvent. m.p 206° C.; $[\alpha]_D^{20}$+29.3° (c=1.0 in $CHCl_3$). The purity of the product is 99.5% area by HPLC, containing Impurity A 0.1% area by HPLC; Impurity B 0.1% area by HPLC; and Impurity F 0.1% area by HPLC.

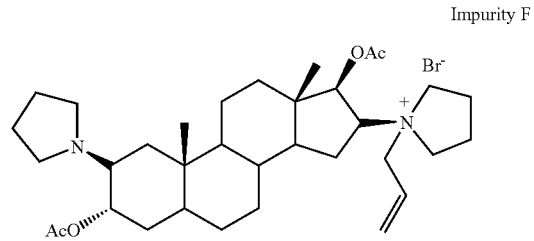

Impurity F

Example 25

Preparation of 1-[17β-acetyloxy-3α-hydroxy-2β-(4-morpholinyl)-5α-androstan-16β-yl]-1-(2-propenyl) pyrrolidinium bromide, Compound I—Base In Situ A glass reactor was charged with 2β-(4-morpholinyl)-16β-(1-pyrrolidinyl)-5α-androstan-3α,17β-diol 17-acetate, Compound VIII, (8.65 Kg, 17.7 mol) and dichloromethane (130 L) at 20-22° C. under $N_2$ atmosphere. Then, 40 L of dichloromethane were distilled at 32-35° C. at normal pressure and the solution was allowed to reach 20-25° C. The volume was replaced with 40 L of dichloromethane and the same volume was stripped at 32-35° C., the mixture was cooled down to 20-25° C. Sodium carbonate (8.65 Kg) was added into the reactor and the resulting mixture was stirred during 5 min. Followed by the addition of allyl bromide (4.28 Kg). The resulting suspension was stirred for 24 hours at 32-35° C. The mixture was then cooled to room temperature (20-25° C.) and filtered under vacuum to remove the salt which was rinsed with dichloromethane (8.65 L). The solvent mixture was removed under vacuum keeping the temperature below 20° C. The oily product obtained was dissolved with dichloromethane (45 L) and concentrated under vacuum keeping the temperature below 20° C.; this procedure was repeated twice. Once again the residue was dissolved at room temperature under nitrogen atmosphere in dichloromethane (86.5 L), and aluminum oxide (4.32 Kg) were added, the resulting mixture was stirred at 20-22° C. during 30 min and then filtered. The solution was slowly added to a glass reactor containing diethyl ether (452 L) with continuous stirring. The resulting suspension was stirred for 30 minutes and filtered under nitrogen atmosphere. The solid obtained was dried at 35° C. at least during 5 days to give 9.70 Kg (0.016 mol, 112.13% w/w yield, 89.88% molar yield) of an off-white solid, having a purity of 99.9% area by HPLC, containing Impurity A 0.1% area by HPLC, and Impurity B 0.1% area by HPLC.

Example 26

Comparative Example

Preparation of 2β-(4-morpholinyl)-16β-(1-pyrrolidinyl)-5α-androstan-3α,17β-diol 17-acetate, Compound VIII, According to Example 7 of U.S. Pat. No. 4,894,369

Acetyl chloride (0.179 mL) was added to a solution of compound VII (1.0 g) in dichloromethane (40 mL) and the reaction was set aside at room temperature for 29 hrs (TLC analysis was performed over the reaction course). The solvent was removed under reduced pressure, and the residue was taken up in dichloromethane (19.4 mL). The solution was washed with 5% sodium carbonate solution (20 mL) and water (2×20 mL), dried (Na$_2$SO$_4$), and evaporated to dryness to yield a gum (1.18 g). The crude product showed an HPLC profile containing compound VIII in a purity of 81.56% area, starting diol, compound VII, in an amount of 5.16% area and the diacetate impurity, compound IX, in an amount of 11.93% area.

Example 27

Comparative Example

Preparation of (2α,3α,5α,16β,17β(3)-2,3-epoxy-16-(1-pyrrolidinyl)androstan-17-ol, Compound IV
According to Example 1 of U.S. Pat. No. 4,894,369

To a suspension of compound III (10 g) in methanol (100 mL) was added a sodium hydroxide solution (10 mL; 4N) at room temperature. The reaction mixture was heated under reflux for 30 minutes. The reaction mixture was then cooled to 40° C. and pyrrolidine (15 mL) was added. The reaction mixture was heated under reflux for 15 minutes. The reaction mixture was cooled to 10° C. and then, sodium borohydride (2 g.) was added. The reaction mixture was heated to room temperature and stirred for two hours. Water was added (200 mL) and the resulting solid was filtered off and washed with water (3×100 mL). The solid was dried under vacuum overnight to give a white product (9.6 g.) having an HPLC purity of: Compound IV (75.12% area), Compound IV-a (11.62% area) and Compound IV-b (4.89% area).

Crystallization of the crude product from acetone (250 mL) afforded 5.3 g of a white solid having an HPLC purity of: Compound IV (92.20% area), Compound IV-a (2.13% area) and Compound IV-b (0.82% area).

Example 28

Preparation of 2α,3α-epoxy-16β-(1-pyrrolidinyl)-5α-androstan-17β-ol, Compound IV Step (a): Synthesis of Compound VI
10 g of 2α,3α,16α,17α-bisepoxy-5α-androstan-17p-ol acetate (28.86 mmols) were dissolved in 100 ml of methanol at 20-22° C. under agitation. Then 8 ml of sodium hydroxide 4N (32 mmols) were added. The mixture was then warmed to reflux and maintained at reflux temperature for 30 minutes. The mixture was then cooled to 35° C. and 4.8 ml of pyrrolidine (57.37 mmols ) were added. Then, the mixture was heated to reflux again and maintained at reflux for 2 hours. The mixture was then cooled to 30° C. poured into a flask containing 600 ml of cold water (3-6° C.). The reaction flask was washed with 20 ml of methanol, which was then poured into the flask into which the reaction mixture was poured. The mixture was then maintained with stirring at 3-6° C. for 40 minutes. The resulting solid was then collected by filtration and washed with 40 ml cold water. The solid was then dried on the filter with suction for at least 12 hours and the wet solid was used in the next step. Obtained: 9.5 g wet of VI mixture with VI-a in a 86:14 ratio.

Step (b): Isomer Equilibration of Compound VI
9.5 g of the wet solid mixture of VI and VI-a obtained in step (a) were suspended into 47.5 ml of methanol (5 vol), then the mixture was heated to reflux temperature and maintained at reflux for 20 minutes. Then over a period of about 90 minutes were slowly added 142.5 ml of water (15 vol), allowing the reflux temperature to rise during the addition. Afterwards, the mixture was maintained with stirring for an additional 30 minutes at reflux temperature. Then the mixture was cooled to 0-5° C. over a period of about 45 minutes. The solid was then collected by filtration and then washed with 38 ml of water. The solid was kept on the filter under suction for 12 hours and then used in the next step. Obtained: 8.8 g of VI in an enriched isomeric ratio of 98.2:1.8.

Step (c): Reduction to Compound VI to Compound IV
In a flask, under nitrogen atmosphere, load 8.8 g of VI (enriched isomeric ratio), 88 ml of methanol (10 vol) and 44 ml of Dichloromethane (5 vol). The mixture was then stirred at 20-25° C. until complete dissolution was achieved. The resulting solution was cooled to 0-5° C. and then 1.70 g of sodium borum hydride (45 mmols) was added portion-wise over a period of about 10 minutes. The resulting mixture was then warmed to 20-25° C. over a period of about 90 minutes and maintained with stirring for an additional 60 minutes.

Then some of the solvents were distilled off under vacuum at an internal temperature of less than or equal to 40° C., until a residual volume of 79.2 ml was achieved. 35.2 ml of methanol was then added to the mixture. Then the solvents are distilled off under vacuum, until a residual volume of 79.2 ml was achieved. The mixture was then warmed to 25° C. and 352 ml of demineralized water was added under agitation over a period of about 1 hour. The resulting suspension was then cooled to −2/+2° C. over a period of at least 30 minutes, and the suspension was maintained under agitation at this temperature for an additional 90 minutes. The solid was then collected by filtration and the filter cake washed with 35 ml demineralized water. After drying (16 hrs, 40° C., under vacuum) 8.3 g of IV were obtained (yield 80.6%) This sample showed 0.83% of IV-a; 0.49% of IV-b; 1.91% of IV-c; total unknown 3.3%.

Step (d): Final Purification of Compound IV

Under nitrogen, 8.3 g of IV from step (c) were loaded in a flask and, 104 ml of dichloromethane were added. The mixture was then heated to 30° C. until complete dissolution was achieved. 7.0 ml of 0.01M HCl was then added to the mixture and the mixture was stirred for 30 minutes to complete the extraction. The aqueous layer was separated from the resulting biphasic system and discarded. The organic layer was washed with 2.4 ml of 0.1M HCl, and the aqueous layer was separated and discarded. The organic layer was then washed with 2.5 ml of water, and the aqueous layer was separated and discarded. The organic layer was then heated to reflux temperature, and about 71 ml of the solvents were distilled from the organic layer over a period of about 1 hour. Then 104 ml of methanol were added. The solution was then heated to reflux temperature and about 59 ml of solvents were distilled off over a period of about 1 hour. Then, while maintaining the temperature at about 50° C., 33 ml of demineralized water were added over a period of about 15 minutes. The resulting unclear solution was then cooled to 25° C. over a period of about 1 hour. The solution was then cooled to 0/−2° C. over a period of about 1 hr and maintained at this temperature for 60 minutes. The solid was then collected by filtration and washed with 33ml of demineralized water. After drying the product for 16 Hrs at 40° C. under vacuum, 8.0 g of pure IV were obtained (IV-a 0.10% ; IV-b 0.10%; IV-c 0.58%) Yield 78%

Analysis of 2α,3α-epoxy-16β-(1-pyrrolidinyl)-5α-androstan-17-one, Compound VI and of the equilibration reaction mixture of 2α,3α-epoxy-16α-(1-pyrrolidinyl)-5α-androstan-17-one, Compound VI-a, and 2α,3α-epoxy- 16β-(1-pyrrolidinyl)-5α-androstan-17-one, Compound VI. The HPLC conditions were as follows. The column & packing were X Terra MS C18; 5 μm, 250 mm×4.6 mm catalog no. 18600494 or equivalent. Eluent A was water and eluent B was 100:1 (v/v) methanol:NH$_4$OH. The composition of the eluent was A:B 20:80 (v/v). The stop time was 20 min, flow rate 0.8 mL/min., detector UV at 210 nm, column temperature was 30° C., and the injection volume was 20 μl.

The analysis of 2α,3α-epoxy-16β-(1-pyrrolidinyl)-5α-androstan-17β-ol, Compound IV was performed with a column & packing X Terra MS C18; 5 μm, 250 mm×4.6 mm catalog no. 18600094 or equivalent. The eluent A was water and eluent B was methanol (NH$_4$OH, 28%) 100:1 (v/v). The composition was A:B 20:80 (v/v). The stop time was 45 minutes, the flow rate was 0.8 mL/mins., the detector was UV at 210 nm, the column temperature was 30° C., and the injection volume was 10 μl.

The analysis of 2β-(4-morpholinyl)-16β-(1-pyrrolidinyl)-5α-androstan-3α,17β-diol, Compound VII was performed with a column & packing X Terra MS C18; 5 μm, 250 mm×4.6 mm catalog no. 18600494 or equivalent. Eluent A was water and eluent B was 100:1 (v/v) methanol:NH$_4$OH, the composition was A:B 20:80 (v/v). The stop time was 45 min., the flow rate was 0.8 mL/min., the detector was UV at 210 mn, the column temperature was 30° C., and the injection volume was 20 μl.

The analysis of 2β-(4-morpholinyl)-16β-(1-pyrrolidinyl)-5α-androstan-3α,17β-diol 17-acetate, Compound VIII was performed with a column & packing Hypersil silica; 5 μm, 250 mm×4.6 mm, cat n. 30005-254630 or equivalent. The eluent A was Buffer of tetramethylammonium hydroxide, eluent B was acetonitrile, and the composition was A:B 25:75. The stop time was 20 minutes, the flow rate was 1.0 mL/min., the detector was UV at 210 nm, the column temperature was 30° C., and the injection volume was 10 μl.

Analysis of rocuronium bromide, Compound I, was performed with a column & packing Hypersil silica; 5 μm, 250 mm×4.6 mm, Cat No. 30005-254630 or equivalent. Eluent A was tetramethylammonium hydroxide Buffer, 0.05M, pH 7.4, eluent B was acetonitrile, and the composition was 10:90, A:B. The stop time was 25 min., the flow rate was 2.0 mL/min., the detector was UV at 210 mn, the column temperature was 30° C., and the injection volume was 5 μl.

Example 29

Reference Example

Transformation of Compound VI into Compound IV
(Example 1 of U.S. Pat. No. 4,894,369)

Sodium hydroxide solution (150 ml; 4N) was added to a suspension of (2α,3α,5α,16β,17α)-2,3,16,17-bisepoxy-androstan-17-ol acetate (150 g) in methanol (1.5 l) and the mixture was heated under reflux for 30 min. When the solution had cooled to approx. 40° C., pyrrolidine (225 ml) was added and the solution was heated under reflux for a further 15 min. The solution was cooled to approx. 10° C. by means of an ice-bath, and sodium borohydride (30 g) was added portionwise with stirring, maintaining the temperature below 20° C. The solution was stirred for 2 h. at room temperature, then water (3 l) was added to precipitate the product, which was filtered off and washed with water (3×1l). A solution of the crude solid in dichloromethane (1 l) was washed neutral with water (2×1l), dried (Na$_2$SO$_4$) and evaporated to dryness. Crystallisation of the resulting white solid from acetone afforded (2α,3α,5α,16β,17β)-2,3-epoxy-16-(1-pyrrolidinyl)-androstan-17-ol (85.2 g), m.p. 156°-160° C.; $[\alpha]_D^{20}$+ 33.6° (c 1.05 in CHCl$_3$)

Example 30

Reference Example

Transformation of Compound IV into Compound
VII (Example 3 of U.S. Pat. No. 4,894,369)

Water (50 ml) was added to a solution of (2α,3α,5α,16β, 17β)2,3-epoxy-16-(1-pyrrolidinyl)-androstan-17-ol (85.2 g) in morpholine (500 ml) and the reaction mixture was heated at reflux temperature for 3 d. Evaporation of the reaction mixture gave a crude product, which was crystallised from acetone. Recrystallisation from methanol gave pure (2β,3α, 5α,16β,17β)-2(4-morpholinyl)-16-(1-pyrro lidinyl)-androstane-3,17-diol (71.2 g), m.p. 212°-219° C.; $[\alpha]_D^{20}$=+87.9° (c 1.02 in CHCl$_3$).

Example 31

Reference Example

Transformation of Compound VII into Compound
VII (Example 7 of U.S. Pat. No. 4,894,369)

Acetyl chloride (9.63 ml) was added to a solution of (2β, 3α,5α,16β,17β)-2-(4-morpholinyl)-16-(1pyrro lidinyl)-androstane-3,17-diol (53.5 g) in dichloromethane (2.14 l) and the reaction was set aside at room temperature for 18 h. The solvent was removed under reduced pressure, and the residue was taken up in dichloromethane (500 ml). The solution was washed with 5% sodium carbonate solution (500 ml) and water (2×500 ml), dried (Na$_2$SO$_4$), and evaporated to dryness to yield a gum (59.9 g), which was chromatographed on alumina (Fluka type 5016A) (50 g). Crystallisation of the material, from pure fractions, from diethyl ether-n-hexane afforded (2β,3α,5α,16β,17β)-2-(4-morpholinyl)-16-(1-pyrrolidinyl)-androstane-3,17-diol 17-acetate (28.0 g), m.p. 149°-153° C. $[\alpha]_D^{20}$=+54.0° (c 1.03 in CHCl$_3$).

Example 32

Reference Example

Transformation of Compound VIII into Compound I (Example 23 of U.S. Pat. No. 4,894,369)

2-propenyl bromide (1.95 ml) was added to a solution of (2β,3α,5α,16β,17β)-2-(4-morpholinyl)-16(1-pyrro lidinyl)-androstane-3,17-diol 17-acetate (1.35 g) in dichloromethane (27 ml) and the solution was sealed in a pressure bottle at room temperature for 22 h. The solvent was removed under reduced pressure with the minimum of heating and the crude solid (1.59 g) was chromatographed on alumina (Fluka type 5016A). The pure fractions were combined, taken up in dichloromethane (15 ml) and diethyl ether (100 ml) was added to precipitate pure 1-[(2β,3α,5α,16β,17β)-17-acetyloxy-3-hydroxy-2-(4-morpholinyl)-androstan-16-yl]-1-(2propenyl)-pyrrolidinium bromide (1.14 g), m.p. 161°-169° C.; $[\alpha]_D^{20}$=+18.7° (c 1.03 in CHCl$_3$).

What is claimed is:

1. A process for the preparation of the quaternary ammonium salt, Rocuronium bromide, of formula I

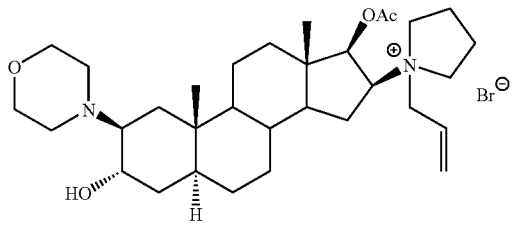

comprising:
(a) combining a starting Compound VI having about 10% to about 40% area by HPLC of Compound VI-a with a water miscible organic solvent to obtain a suspension;
(b) stirring the suspension at a temperature of about 60° C. to about 80° C. to obtain a mixture;
(c) adding water to the mixture;
(d) isolating Compound VI from the mixture, wherein the isolated Compound VI has less than about 3% area by HPLC of Compound VI-a;
(e) forming a solution of Compound VI having less than about 3% of compound VI-a, and a water miscible organic solvent optionally combined with a water immiscible organic solvent;
(f) adding at least one reducing agent to the solution at a temperature of about −15° C. to about 10° C. to obtain a mixture;
(g) stirring the mixture at a temperature of about 20° C. to about 24° C.;
(h) isolating Compound IV from the mixture having a purity of at least 85% area by HPLC;
(i) forming a suspension of Compound IV, morpholine, and at least one acid catalyst;
(j) stirring the suspension at a temperature of about 100° C. to about reflux for about 24 hours to about 48 hours;
(k) isolating Compound VII from the suspension;
(l) combining Compound VII, a polar organic solvent, and at least one acetylating reagent with at least one base to obtain a mixture;
(m) isolating Compound VIII from the mixture;
(n) combining Compound VIII, a polar aprotic organic solvent, allyl bromide, and at least one inorganic base to obtain a mixture;
(o) and isolating rocuronium bromide from the mixture.

2. A process for preparing rocuronium bromide from compound VIII comprising:
(a) combining Compound VIII, a polar aprotic organic solvent, allyl bromide, and at least one inorganic base to obtain a mixture; and
(b) isolating rocuronium bromide from the mixture.

3. The process according to claim 2, wherein the polar aprotic organic solvent is selected from the group consisting of: halogenated hydrocarbon, ester and ketone.

4. The process according to claim 2, wherein the polar aprotic organic solvent is selected from the group consisting of $C_{1-2}$ halogenated hydrocarbons, ethyl acetate, and $C_{3-4}$ ketones.

5. The process according to claim 2, wherein the polar aprotic organic solvent is acetone.

6. The process according to claim 2, wherein the polar aprotic organic solvent is dichloromethane.

7. The process according to claim 2, wherein the allyl bromide is present in an amount of about 1.3 to about 3 mole equivalents per mole of compound VIII.

8. The process according to claim 2, wherein the mixture obtained in step (a) has a water content of less than about 0.1% determined by Karl Fischer titration.

9. The process according to claim 2, wherein the inorganic base is selected from the group consisting of alkaline and aluminum bases.

10. The process according to claim 2, wherein the inorganic base is selected from the group consisting of sodium carbonate, sodium bicarbonate, potassium carbonate, and aluminum oxide.

11. The process according to claim 1, wherein the inorganic base is sodium carbonate.

12. The process according to claim 1, wherein the mixture in step (b) is stirred at a temperature of about 15° C. to about 40° C., prior to isolating Rocuronium bromide.

13. The process according to claim 1, wherein Crude Roc of formula I is purified by a process comprising:
a) dissolving the crude rocuronium bromide in a polar aprotic organic solvent to form a solution;
b) adding a decolorizing agent optionally combined with a base to the solution to form a first suspension;
c) filtering the first suspension;
d) adding the filtrate to an anti-solvent and vigorously stirring to obtain a second suspension;
e) recovering wet solid of Rocuronium bromide from the second suspension; and
f) drying the wet Rocuronium bromide at a temperature of no more than about 35° C.

* * * * *